US012754163B2

(12) United States Patent
Járvás et al.

(10) Patent No.: US 12,754,163 B2
(45) Date of Patent: Oct. 6, 2026

(54) INTEGRATED METHOD FOR URINARY PROSTATE SPECIFIC ANTIGEN N-GLYCOSYLATION PROFILING BY CAPILLARY ELECTROPHORESIS

(71) Applicant: PANNON EGYETEM, Veszprém (HU)

(72) Inventors: Gábor Járvás, Veszprém (HU); Balázs Reider, Veszprém (HU); Hajnalka Jankovics, Balatonalmádi (HU); Ferenc Vonderviszt, Veszprém (HU); András Guttman, Budapest (HU)

(73) Assignee: Pannon Egyetem, Veszprém (HU)

( * ) Notice: Subject to any disclaimer, the term of this patent is extended or adjusted under 35 U.S.C. 154(b) by 87 days.

(21) Appl. No.: 18/569,454

(22) PCT Filed: Jun. 16, 2022

(86) PCT No.: PCT/HU2022/050052
§ 371 (c)(1),
(2) Date: Dec. 12, 2023

(87) PCT Pub. No.: WO2022/263873
PCT Pub. Date: Dec. 22, 2022

(65) Prior Publication Data

US 2024/0272117 A1 Aug. 15, 2024

(30) Foreign Application Priority Data

Jun. 16, 2021 (HU) .................................... P2100233

(51) Int. Cl.
*G01N 27/447* (2006.01)
*C07K 1/22* (2006.01)
*C12Q 1/40* (2006.01)
*G01N 33/58* (2006.01)
*G01N 33/68* (2006.01)

(52) U.S. Cl.
CPC ............. *G01N 27/447* (2013.01); *C07K 1/22* (2013.01); *C12Q 1/40* (2013.01); *G01N 33/582* (2013.01); *G01N 33/6893* (2013.01); *G01N 2333/4728* (2013.01); *G01N 2400/10* (2013.01)

(58) Field of Classification Search
CPC .. G01N 27/447; G01N 27/26; G01N 27/4479; G01N 27/44721; G01N 33/6893; G01N 33/68; G01N 33/582; G01N 33/57434; G01N 33/50; C12Q 1/40; A61K 35/52
See application file for complete search history.

(56) References Cited

U.S. PATENT DOCUMENTS

2004/0147033 A1 7/2004 Shriver et al.

OTHER PUBLICATIONS

Audenhove, Isabel et al: "Nanobodies as Versatile Tools to Understand, Diagnose, Visualize and Treat Cancer", EBIOMEDICINE, vol. 8, Jun. 1, 2016 (Jun. 1, 2016), pp. 40-48.
Crauwels, Maxine et al., New Biotechnology vol. 57. Jan. 27, 2020 pp. 20-28.
Gonzalez-Sapienza, Gualberto et al. Frontiers in Immunology. vol 8, Aug. 21, 2017 Article 977 pp. 1-12.
Kammeijer, Guinevere et al: "An In-Depth Glycosylation Assay for Urinary Prostate-Specific Antigen", Analytical Chemistry, vol. 90, No. 7, Mar. 4, 2018 (Mar. 4, 2018), pp. 4414-4421.
Kammeijer, Guinevere et al: "Sialic acid linkage differentiation of glycopeptides using capillary electrophoresis—electrospray ionization—mass spectrometry", Scientific Reports, 7, Article No. 3733 (2017), Jun. 16, 2017 (Jun. 16, 2017), pp. 1-10.
Laroy, Wouter et al: "Glycome mapping on DNA sequencing equipment", Nature Protocols, Nature Publishing Group, GB vol. 397, No. 1 Jun. 27, 2006 (Jun. 27, 2006), pp. 397-405.
Lu, Grace et al: "Capillary Electrophoresis Separations of Glycans", Chemical Reviews, vol. 118, No. 17, Mar. 12, 2018 (Mar. 12, 2018), pp. 7867-7885.
Reider, Balázs et al. "Separation based characterization methods for the N-glycosylation analysis of prostate-specific antigen", Journal of Pharmaceutical and Biomedical Analysis; vol. 194, Nov. 25, 2020, p. 113797, Part: "Separation based characterization methods for PSAN-glycosylation".
Reider, Balázs et al: "Integrated workflow for urinary prostate specific antigen N-glycosylation analysis using sdAb partitioning and downstream capillary electrophoresis separation", Analytica Chimica Acta, vol. 1184 (2021) p. 338892.
Szigeti, Márton & Guttman, András: Nature Scientific Reports. vol. 7, Sep. 15, 2017 p. 11663.
Vermassen, Tijl et al: "Capillary electrophoresis of urinary prostate glycoproteins assists in the diagnosis of prostate cancer", Electrophoresis, Verlag Chemie, Hoboken, USA, vol. 35, No. 7, Dec 20, 2013 (Dec 20, 2013), pp. 1017-1024.

*Primary Examiner* — Gurpreet Kaur
(74) *Attorney, Agent, or Firm* — Daniel S. Kim

(57) ABSTRACT

In the present invention a method is provided for capillary electrophoresis-based (CE-based) comprehensive N-glycan analysis of urinary PSA. The method is useful for analysis of PSA glycans from urine and for diagnosis of PSA-related conditions.

12 Claims, 22 Drawing Sheets

INTEGRATED METHOD FOR URINARY PROSTATE SPECIFIC ANTIGEN N-GLYCOSYLATION PROFILING BY CAPILLARY ELECTROPHORESIS

This is the national stage of International Application PCT/HU2022/050052, filed Jun. 16, 2022.

FIELD OF THE INVENTION

In the present invention a method is provided for capillary electrophoresis-based (CE-based) comprehensive N-glycan analysis of urinary PSA. The method has proved to be effective and still mild so that PSA glycans remain intact to provide a reliable analysis.

TECHNICAL BACKGROUND

Prostate cancer represents the second highest diagnose rate in men regarding all cancer diagnoses worldwide. The development and progression of prostate cancer is not completely discovered at molecular biology level but it is suggested that N-glycan profiles change during tumor genesis.

Today, prostate cancer (PCa) has the second highest diagnose rate in men with 21% of all cancer diagnoses worldwide (Carlsson & Vickers, 2020). Currently, the gold standard biomarker for PCa is serum prostate specific antigen (PSA). PSA, also known as human kallikrein 3 (KLK3 or hK3), is an organ-specific glycoprotein, which plays an important role in the liquefaction of semen (Armbruster, 1993). PSA is produced by the prostate epithelial cells and it is secreted primarily into the prostate but it is also presented in other body fluids, like urine. Certain diseases, like PCa or benign prostate hyperplasia and surgeries or biopsies can cause an elevated PSA level in the bloodstream (Pinsky et al., 2006). Serum PSA assays greatly reduced the mortality rate of PCa, but the number of false positive diagnoses steeply increased (Carlsson & Vickers, 2020). To overcome the lack of specificity, the search for better PCa biomarkers has been intensified in the last decades (Filella et al., 2018). As in numerous other cancer cases, protein glycosylation seemed to be a promising target of investigation (Adamczyk et al., 2012). The link between PCa and changes in PSA glycosylation has been reported in several studies (Gilgunn et al., 2013; Munkley et al., 2016; Tkac, Bertok, et al., 2019; Tkac, Gajdosova, et al., 2019a). The most common cancer-associated glycosylation-related alterations were found in sialylation (especially α2,3-sialylation) (Saldova et al., 2011), fucosylation (mainly core fucosylation, i.e., addition of fucose to the innermost GlcNAc residue in the vicinity of the polypeptide backbone), O-glycan truncation (presence of shortened O-glycans), branching of N- and O-glycans (i.e., due to increased activity of N-acetylglucosaminyltransferase) and the presence of polysialic acid (dos Santos Silva et al., 2019; Ferens-Sieczkowska et al., 2013; Gilgunn et al., 2020; Kyselova et al., 2007; Tkac, Gajdosova, et al., 2019b).

To detect any of the glycosylation alterations, a wide repertoire of bioanalytical tools has been utilized. Numerous lectin-based biosensors have been developed to separate certain sugar structures (e.g., α2,6- and α2,3-sialylation) (Pihíková et al., 2015) and instrumental analysis has also applied mass spectroscopy, liquid chromatography, capillary electrophoresis, or their various combinations for PSA glycan analysis (Reider et al., 2020). Albeit the glycosylation of PSA was extensively studied, only a few reported methods were able to achieve full glycan mapping or separate the critical structures and these techniques usually required special components or complex instrumentation (Kammeijer et al., 2018; Tkac, Gajdosova, et al., 2019a). The biological source of PSA is also critical. Semen, blood, and urine are the most commonly used body fluids for this purpose. Standard, commercially available PSA is obtained from human semen, as it contains PSA in the highest concentration (approximately 1.3 mg/ml) (Lynne et al., 1999), but semen usage in clinical analysis is very limited. Blood is much easier to collect (even though it is an invasive procedure), therefore it is frequently applied as a viable sample source. Unfortunately, the PSA concentration in blood is usually very low (<10 ng/ml), which can make extensive qualitative analysis problematic. Urine contains PSA in a higher dose (~100 ng/ml (Bolduc et al., 2007)), but its concentration can change on a very large scale. Urine has another upside, compared to blood and semen, that its matrix possesses a lower glycoprotein content, which otherwise could interfere with certain glycan analysis.

To obtain appropriate analytical results, sample preconcentration is often required due to the limiting sample concentration. Capturing PSA from the biological matrix is also beneficial for sensitive methods to filter any non-PSA related sugar or protein impurities, which could corrupt the analysis. Monoclonal antibodies are commonly used capturing agents (Vashist & Luong, 2018), but their accessibility can limit their application and they are glycoproteins, therefore their removal from the sample prior to analysis is often necessary to avoid any possible interference. Single domain antibodies (sdAbs) (or nanobodies) can alleviate this drawback (Arbabi-Ghahroudi, 2017). They are much smaller in size, can be readily produced in bacteria and do not contain sugar moieties. Also, different linker tags (e.g., 6-histidine tag) can be attached to them to facilitate their immobilization to various surfaces.

WO2011074802A2 (Yoon et al., 2011) describes a kit for diagnosing prostate cancer and a diagnosis method. In this invention, an antibody against a prostate-specific antigen (PSA) is used to detect PSA from human urine sample. The PSA-specific antibody may be a monoclonal antibody, a polyclonal antibody or fragments thereof capable of binding to PSA. The antigen and antibody forms an immunological complex, which can be detected by immunoassays, like immunochromatography, ELISA, immunohistochemistry, etc. In this invention, the glycosylation of PSA is not detected, nor is it mentioned as a potentially important part of the detection.

WO2017077162A1 (Peracaula Miró et al., 2017) describes a method for in vitro differential diagnosis of prostate cancer. The method comprises partially purifying PSA in a fluid sample from a subject, and then determining the percentage of sialic acid α2,3 of PSA and/or the proportion of internal fucosylation of the PSA. The method may be used to distinguish between high-risk prostate cancer and low- or intermediate-risk prostate cancer patients. The sample can be whole blood, serum, plasma and urine. The percentage of PSA comprising sialic acid α2,3 is determined by affinity chromatography. They do not use capillary electrophoresis (although polyacrylamide electrophoresis (SDS-PAGE) is used to isolate PSA from different fractions).

WO2017130578A1 (Yoneyama et al., 2017) (see also EP3410118A1) teaches a novel prostate cancer (PCa), specifically prostate carcinoma determination method and a PCa malignancy determination method based on PSA glycan analysis. The method comprises determining the ratio of the amount of free prostate specific antigen, which has a glycan in which the terminal sialic acid residue of the glycan is + (2,3)-linked to a second galactose residue from the terminal of the glycan, to the amount of free PSA in a biological sample, and then determining that prostate carcinoma is developed or the probability of developing prostate carcinoma is high in the case where the ratio is 40% or higher. In a further developed version of the invention, however, WO2019221279A1 (Yoneyama et al., 2019) (see also EP3796001A1) teaches that, so as to obtain a diagnosis of prostate carcinoma, a second ratio is to be obtained between the first ratio and a volume of the prostate of the subject; and determining prostate carcinoma based on the obtained second ratio.

WO2010011357A2 (Zhang et al., 2010) teaches a method of determining whether a subject has prostate cancer, said method comprising determining if the subject has an altered PSA glycosylation pattern as compared to the glycosylation pattern of PSA from a healthy subject, wherein the glycosylation pattern is α2,3-linked sialylation or α2,6-linked sialylation of PSA. In this method, however, gel electrophoresis and not capillary electrophoresis is used.

In WO2004066808 (Shriver et al., 2004) a method is disclosed for evaluating the clinical status of a subject in a sample comprising a pre-selected target glycoprotein typically PSA; and determining the glycoprofile of PSA using a method that can detect it in amounts less than 1000 ng/ml, wherein the glycoprofile indicates that the subject has a predefined clinical status. Determining the glycoprofile comprises detecting alterations in BI-6 branching structures, of one or more of N-linked and O-linked oligosaccharides, and/or comprises detecting one or more of alterations in Lewis antigens, sialylation, and fucosylation. The use of capillary electrophoresis is said to be advisable, however, the actual examples are carried out with mass spectrometry. Urine is mentioned among others as a possible source of the glycoprotein but is not analysed actually. As a preliminary purification magnetic beads are applied.

Reider et al. (Reider et al., 2020) review separation based characterization methods for the N-glycosylation analysis of prostate-specific antigen including CE-LIF methods. The authors conclude that CE-LIF methods may lack high reproducibility mainly due to changes in the properties of the capillary inner surface; moreover, the complexity of the required sample preparation methods is also present a problem with CE based separation techniques. Automation may become difficult if multiple sample preparation steps are required.

In this invention a novel workflow is presented for capillary electrophoresis-based (CE-based) comprehensive N-glycan analysis of urinary PSA. The analysis is preceded by a selective, high yield sdAb-based PSA capture and includes various sample concentration steps. Thereafter, the glycans were enzymatically released from the enriched PSA, fluorescently labeled and analyzed by CE. The corresponding glycan structures were identified by their glucose unit (GU) values and endoglycosidase sequencing.

BRIEF DESCRIPTION OF THE INVENTION

The invention relates to a method for PSA-analysis from urine sample, wherein said method comprises the steps of providing urine sample, preparing said urine sample for analysis, separating PSA from said urine sample by affinity separation to obtain enriched PSA, releasing glycans from the enriched PSA to obtain released PSA-glycans, analyzing the released glycans by separation with capillary electrophoresis (CE) wherein detection of the separated released glycans is carried out by fluorescent detection, UV-detection or mass spectrometry (MS).

Preferably preparing said urine sample comprises pre-concentration of the sample.

Preferably affinity separation is carried out by using immobilized anti-PSA binding molecules.

Preferably affinity separation is affinity partitioning. Preferably affinity separation is affinity chromatography.

In a preferred embodiment the released PSA-glycans are prepared for detection, preferably labeled, preferably labeled by a fluorophore for fluorescent detection.

In a preferred embodiment detection of the separated released glycans is carried out by fluorescent detection, wherein between the releasing step and the analyzing step the following step is carried out:

labeling the released PSA glycans by a fluorescent dye, to obtain fluorophore labeled released PSA glycans, and the fluorophore labeled glycans are detected.

Preferably said method comprises the steps of providing urine sample, preparing said urine sample for analysis (pre-concentration), separating PSA from said urine sample to obtain enriched PSA by, providing an affinity partitioning column comprising immobilized anti-PSA binding molecules, affinity partitioning of PSA from the matrix of the urine sample by using the affinity partitioning column, to obtain enriched PSA, releasing glycans from the enriched PSA to obtain released PSA-glycans, labeling the released PSA glycans by a fluorescent dye, to obtain fluorophore labeled released PSA glycans, analyzing the fluorophore labeled released glycans by separation with capillary electrophoresis (CE) wherein detection of the separated labeled released glycans is carried out by fluorescent detection.

Preferably the binding molecules are nanobodies, in particular single-domain antibodies.

In an alternative embodiment the detection is carried out by UV-detection or mass spectrometry (MS). In an embodiment detection is carried out by taking spectra, e.g. MS spectra. In an embodiment UV-detection is carried out at one or more wavelength either in absorbance or transmittance mode, preferably in absorbance mode.

Preferably the sample is a urine sample of a male mammal, preferably a human, more preferably a male human.

Preferably preparing the urine sample includes pre-concentration.

Preferably the affinity partitioning column comprises nanobodies, in particular single-domain antibodies as binding molecules.

In the method of the invention preferably the binding molecules are single domain antibodies.

Preferably the binding molecules, preferably the single domain antibodies have a dissociation constant $K_d$ which is not higher than 30 nM, preferably not higher than 20 nM, more preferably not higher than 10 nM, preferably not higher than 5 nM.

Alternatively the binding molecules are capturing agents.

Preferably the binding molecules are non-glycosylated.

In the method of the invention preferably the affinity partitioning column is a chromatography microcolumn, wherein preferably the nanobodies have a tag, preferably a histidine tag and the column has matrix binding tags, preferably histidine tags, preferably a Ni-IMAC microcolumn.

Preferably releasing glycans from the PSA to obtain released PSA-glycans is carried out chemically or enzymatically, preferably with endoglycosidases.

In a preferred embodiment of the invention the method comprises analyzing the fluorophore labeled released PSA glycans by separating at least the fucosylated and non-fucosylated glycan structures of the fluorophore labeled released PSA glycans. In a preferred embodiment of the invention the method comprises analyzing the fluorophore labeled released PSA glycans by separating at least the α2,3- and α2,6-sialylated isomers of the fluorophore labeled released PSA glycans.

In the method of the invention preferably during CE separation the PSA-glycans are detected by laser induced fluorescence detection.

In alternative embodiments the glycans can be detected by UV-detection or by MS as defined above.

In the method of the invention preferably as a negative control female urine of the same species is applied.

In the method of the invention preferably as a positive control PSA-glycoprotein spiked female urine of the same species is applied.

Optionally the method of the invention also comprises measuring the level of said fucosylated and non-fucosylated structures in the fluorophore labeled released PSA glycans sample, and thereby urine sample, and/or measuring the level of said α2,3- and α2,6-sialylated isomers in the fluorophore labeled released PSA glycans sample, and thereby their level is analysed, preferably determined in the urine sample.

In a further embodiment the method of the invention also comprises measuring a glycosylation pattern of the fluorophore labeled released PSA glycans, including contribution of each individual structure.

In a preferred embodiment of the invention the method comprises analysis of the fluorophore labeled released PSA glycans, comprises separating at least sialylated and optionally non-sialylated PSA-glycans, and optionally measuring the level of said sialylated and optionally non-sialylated PSA-glycans.

In a preferred embodiment of the invention the method comprises analyzing the fluorophore labeled released PSA glycans, comprises separating alpha-2,3-sialylated PSA-glycans, wherein an altered level of alpha-2,3-sialylated PSA glycans as compared to the level of alpha-2,3-sialylated PSA glycans from a healthy subject is indicative of a PSA related disease, in particular prostate cancer.

Preferred and further embodiments regarding the level of alpha-2,3-sialylated PSA-glycans and related diagnostic methods are disclosed in the Detailed description of the invention.

In a preferred embodiment of the invention the method comprises analysis of the fluorophore labeled released PSA glycans, comprises separating at least fucosylated and non-fucosylated PSA-glycans, and optionally measuring the level of said fucosylated and non-fucosylated PSA-glycans.

In an embodiment, an elevated level of fucosylated PSA-glycans as compared to the level of fucosylated PSA glycans from a healthy subject is indicative of a PSA related disease, in particular prostate cancer.

Preferred and further embodiments regarding the level of fucosylated PSA-glycans and related diagnostic methods are disclosed in the Detailed description of the invention.

The invention also relates to a diagnostic method for diagnosing PSA-related condition from urine sample of a subject, preferably of a male subject, said method comprising the steps of carrying out the method for PSA-analysis (PSA-analysis method) of the invention, determining a glycosylation pattern according to the invention in the sample of a patient (patient glycosylation pattern), comparing the glycosylation pattern with a normal glycosylation pattern, and if there is a difference between the patient glycosylation pattern and the normal glycosylation pattern the patient is considered as having a PSA-related condition.

Preferably the normal glycosylation pattern is a healthy glycosylation pattern. A healthy glycosylation pattern is a glycosylation pattern obtained from or typical of a healthy person (optionally a person without any known PSA related condition). Preferably a healthy glycosylation pattern is defined or obtained by analyzing the glycosylation pattern of a plurality of healthy persons (optionally persons without any known PSA related condition) wherein for each glycan of importance a range is defined which is typical of a healthy person. The range for a given glycan can be defined by statistical methods, e.g. by finding a statistical distribution for the levels measured in healthy persons for that given glycan, finding and discarding outliers, optionally re-evaluating the statistics and based thereon defining a range wherein values for levels of the given glycan within the range are considered as typical of a healthy person. A set of such ranges for a plurality of glycans is considered a normal or healthy glycosylation pattern.

In an embodiment the glycosylation pattern may comprise one or more ratio of one or more glycan levels and a reference level. A reference level may be the level of a reference protein, a reference glycan, or a composite level obtained from the levels of multiple glycans, e.g. the total level of plurality of glycans or the total glycan level or a total PSA level.

In a preferred embodiment the diagnostic method comprises determining α2,3-sialylated and optionally α2,6-sialylated isomers in the urine sample. The α2,3-sialylated and optionally α2,6-sialylated isomers preferably relate to PSA-glycans in the sample.

In a preferred embodiment the diagnostic method comprises determining fucosylated and optionally non-fucosylated structures in the urine sample.

The fucosylated and optionally non-fucosylated structures preferably relate to PSA-glycans in the sample.

A preferred embodiment of the diagnostic method of the invention comprises measuring the total glycosylation pattern of the fluorophore labeled released PSA glycans, including contribution of each individual structure comparing the level to healthy control if the level is different from a normal level or normal glycosylation pattern, finding that the subject has a PSA-related condition or disease.

In the method of the invention the control is defined by the glycan pool of healthy control.

In a preferred embodiment a standard (female urine spiked with PSA) is used as a positive control.

In a preferred embodiment a standard (non-spiked female urine) is used as a negative control.

In a particular embodiment the normal glycosylation pattern is a reference glycosylation pattern typical of a healthy subject.

Preferably the sample is a urine sample of a male mammal, preferably a human, more preferably a male human.

In a particular embodiment healthy is understood as the glycan level obtained from a person or plurality of persons without known PSA related condition.

Definitions

A "subject" as used herein is an individual of a mammal having prostate and a urinary system.

The term "mammal" is known in the art and relates to an animal species of which the female feeds her young on milk from her own body, and exemplary mammals include humans, primates, livestock animals (including bovines, porcines, goats, sheeps, horses, etc.), companion animals (e.g., canines, felines, etc.) and rodents (e.g., mice and rats) all or any of which is contemplated herein.

A "patient" is a subject who is or is intended to be under medical or veterinarian observation, supervision, diagnosis or treatment.

The term "binding molecule" is meant herein as a molecule that specifically binds to the target molecule with a desired binding affinity, i.e. with a binding affinity sufficient to form a complex between the binding molecule and the target molecule. In an embodiment the binding molecule carries or comprises an antibody binding part having a complementarity determining region (CDR). Such binding parts can be inserted into a natural or synthetic scaffold molecule. A binding molecule can be derived from a naturally occurring molecule, e.g. from an antibody. In an embodiment the binding molecule is an antibody or a fragment thereof. Binding molecules also include proteins of antibody derived protein scaffolds, like antibody fragments, single-domain antibodies, single chain antibody fragments (scFv), Fab fragments, nanobodies etc. Nanobodies are preferred. Alternatively, a binding molecule can be entirely artificially made, e.g. as a synthetic peptide.

The term "antibody" is meant to refer to a polypeptide ligand substantially encoded by an immunoglobulin gene or immunoglobulin genes.

The term "separating a desirable compound from" one or more other compounds is understood herein as causing to remove certain components from a mixture and causing the desirable compound to be apart from the removed parts. Preferably, when separating said compound from other compounds, e.g. a mixture of compounds, said compound is present in a mixture before the separation and is free of other compounds of the mixture after the separation. The more other compounds the desired compound is free of, the separation is more successful.

In a preferred embodiment or a preferred step the desirable compound is a protein, e.g. glycoprotein, preferably PSA. In this case the term "separating a protein from" or "separating PSA from" other proteins or contaminants is used, mutatis mutandis.

In a further preferred embodiment or a preferred step the desirable compound is a glycan; in this case the term "separating a glycan" means herein separating said glycan from other glycans, e.g. a mixture of glycans, wherein said glycan is present in a mixture before the separation and is free of other glycans of the mixture after the separation.

A separation technique is a method, used for separating a desirable compound from one or more other compounds, wherein said method utilizes a difference in physical and/or chemical property of the desirable compound and of the one or more other compounds, preferably a difference in binding properties to a binding partner, preferably specific binding property to a given binding partner, preferably affinity to a given binding partner.

The term "enriching" relates to increasing the proportion of a desirable compound in a mixture.

The term "purifying a desirable compound" from a mixture (original or starting mixture) is understood herein as providing the desirable compound, after the purification step, in a higher level of purity, i.e. the resulting mixture comprises the desirable compound and comprises less contaminating compounds i.e. a lower proportion of non-desirable, i.e. contaminating compounds than the original (starting) mixture. The level of purity relates to the proportion of the desirable compound relative to the amount of the desirable and non-desirable compounds together.

In a particular aspect purifying a desirable compound is carried out by separating a desirable compound from one or more other compounds. In a particular aspect the resulting mixture is enriched in the desirable compound relative to the original (starting) mixture. In a preferred embodiment a high level of purity of the desirable compound is arrived at by purification.

In the present disclosure a method step defined by separation can be reworded by using the term enrichment in consideration of the definitions herein, mutatis mutandis.

In the present disclosure a method step defined by separation can be reworded by using the term purification in consideration of the definitions herein, mutatis mutandis.

The term "affinity separation" relates to a separation technique based on binding interaction (or binding in short), preferably specific binding interaction, between a desirable compound, preferably a protein, e.g. a glycoprotein, and a binding partner, preferably another macromolecule, e.g. another protein. Specific binding (or affinity) is understood herein as a binding stronger to a given binding partner than to another set of macromolecules e.g. another set of proteins.

Thus, the concept of an 'affinity' separation results from a naturally occurring property of each biological macromolecule which contain a unique set of intermolecular binding forces, existing throughout its internal and external structure and the fact that when alignment occurs between a specific site of these forces in one macromolecule with the site of a set of forces existing in another (different) molecule (binding partner), e.g. macromolecule, an interaction (attractive interaction, i.e. binding) can take place between them.

Affinity separation used in the present invention can be affinity partitioning e.g. affinity chromatography.

The term "affinity partitioning" is a separation method for proteins containing specific binding sites from a mixture of proteins in a medium or matrix, wherein a desirable protein is separated utilizing its specific binding property to a binding partner wherein separation is carried out using an at least two-phase system wherein there is at least one fluid (preferably liquid) phase which can move relative to another phase which comprises a binding partner present in or on a second phase but contacting with the non-bound (free) fluid (preferably liquid) phase. In an embodiment the binding partner is coupled to an appropriate carrier which may form a solid phase. In an embodiment the binding partner is present in another fluid (preferably liquid) phase. In an embodiment the system comprises both a carrier (solid phase) and another fluid (preferably liquid) phase the two comprising the binding partner which is contacted the free fluid (preferably liquid) phase. Preferably the free fluid phase is moving. Preferably the another liquid phase is stationary, preferably is attached to the appropriate carrier which may form a solid phase.

The term "affinity chromatography" is an "affinity partitioning" method carried out in a chromatography column wherein the free fluid phase is a moving phase and the stationary phase comprises a solid carrier which is part of the other phase(s), e.g. is standing phase.

The term "affinity partitioning of PSA" means herein partitioning PSA from a matrix, wherein PSA is a mixture of PSA-glycoproteins with different glycan structures, present in a matrix, e.g. urine matrix before the partitioning step, wherein partitioning is carried out by a partitioning column capable of reversibly binding PSA (with a different affinity than the affinity the other matrix components are bound with) and wherein after the partitioning of PSA, i.e. the mixture of PSA-glycoproteins is provided free of matrix components.

PSA is partitioned between the binding partner and the free fluid phase which partition is determined by the specific binding to its binding partner thereby it can be separated from a heterogeneous mixture.

A "pool" of compounds is used herein as a mixture of compounds when we consider them as a whole comprising each element of the mixture.

A "matrix" is considered here as an environment of a substance or compound of interest, including physical, chemical or biochemical environment. In an embodiment a matrix is provided with the contribution of human action, e.g. by isolation of a sample or by any other human action. A natural matrix is a matrix which is identical or aimed to be identical with the natural environment of the substance or compound of interest. A urine matrix is for example understood herein as every material i.e. the entirety of a urine sample in which the substance or compound of interest is present.

The term "separating a first glycan from second glycan" means herein that separating said first glycan from the mixture of the first glycan and of the second glycan (wherein in an embodiment further glycans may be present).

A substance (e.g. a compound) of interest is "free of" other substances e.g. other one or more compounds if said other substances are not present or are present only in an insignificant level or amount with said substance of interest.

The term "glycosylation pattern" as used herein is meant to refer to the presentation of glycan structures (oligosaccharides) present in a pool of PSA-glycoproteins. A glycoprofile can be presented, for example, as a plurality of peaks each corresponding to one or more glycan structures present in a pool of PSA. In an embodiment glycosylation pattern is understood as a plurality of ranges of levels of glycans. In an embodiment glycosylation pattern comprising ratio of level(s) of one or more glycans relative to a reference level preferably as defined herein.

The term "prostate-specific antigen (PSA)" is meant to refer to a 33 kDa chymotrypsin like protein that is a member of the human kallikrein gene family. In preferred embodiments, PSA is a protein produced by cells of the prostate gland. In a natural matrix PSA is present in the form of a pool of PSA-glycoproteins wherein multiple types of glycan structures are bound to the PSA-glycoprotein molecules.

PSA is normally present in the blood at very low levels; normal PSA levels are defined as between zero (0) to four (4) ng/ml. Increased levels of PSA may suggest the presence of prostate cancer in men or breast or other cancers in women. Most PSA in the blood is bound to serum protein. A small amount of PSA is not bound to serum protein. PSA in this form is called free PSA.

The term "sample" is meant herein to refer to a substance obtained from a bodily fluid or tissue from a subject, i.e. taken from said bodily fluid or tissue of the subject and optionally processed to prepare for analysis. The sample is obtained preferably from urine. A sample as used herein can be unconcentrated or can be concentrated (i.e. processed by concentration) optionally using standard methods. Thus, a urine sample is obtained from urine of a subject by taking from the urine and optionally processed to prepare said sample for analyses, e.g. by a method of the invention.

The term "sialylated" or "sialylation" refers to covalent modification by one or more sialylic acid moieties. In certain embodiments, sialylation is of PSA. In certain embodiments, sialylation can be a 2,6 linked sialylation of PSA. In other embodiments, sialylation can be a 2,3 linked sialylation of PSA.

Sialyl acids or sialic acids are nine-carbon carboxylated sugars which exist in three primary forms. "Sialylated" refers to covalent modification by one or more sialic acid moieties. The most common is N-acetyl-neuraminic acid (2-keto-5-acetamido-3,5-dideoxy-D-glyc-ero-D-galac-tononulopyranos-1-onic acid (CAS Registry Number®: 114-04-5; often abbreviated as NeuSAc, NeuAc, or NANA). A second common form is N-glycolyl-neuraminic acid (Neu5Gc or NeuGc), in which the N-acetyl group of NeuAc is hydroxylated. A third primary sialic acid is 2-keto-3-deoxy-nonulosonic acid (KDN). In a preferred embodiment the sialic acid is N-acetyl-neuraminic acid.

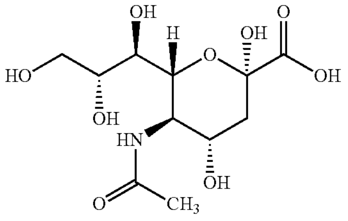

N-acetyl-alpha-neuraminic acid

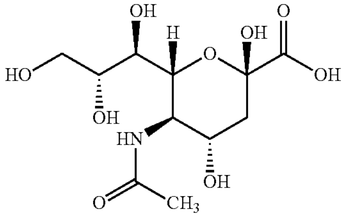

N-acetyl-beta-neuraminic acid

The term "fucosylated" or "fucosylation" refers to covalent modification by a fucose sugar moiety or one or more fucose sugar moieties. "Fucosylation" is a type of glycosylation. In certain embodiments, fucosylation is of PSA.

Fucose is understood herein as L-fucose (CAS Registry Number®: 2438-80-4; (2S,3R,4R,5S)-6-Methyltetrahydro-2H-pyran-2,3,4,5-tetraol, alternative name: 6-Deoxy-L-galactose), which is a hexose deoxy sugar with the following structural formula:

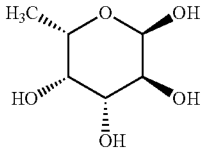

alpha-L-fucose

-continued

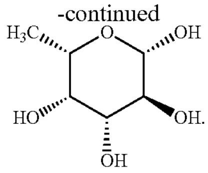

beta-L-fucose

Two structural features distinguish fucose from other six-carbon sugars present in mammals: the lack of a hydroxyl group on the carbon at the 6-position (C-6) (thereby making it a deoxy sugar) and the L-configuration It is equivalent to 6-deoxy-L-galactose.

A “fluorescent” or a “fluorescently labeled” compound as used herein is a compound which can be detected by irradiating with an UV or VIS electromagnetic radiation (“irradiating light”) and the compound absorbs the irradiating light and emits light (emitted light) at another, preferably longer wavelength than that of the irradiating light. Preferably the “detectable fluorescent compound” is capable of fluorescence i.e. emission of light inside of e.g. a cell.

“Detecting” as used herein is understood broadly as obtaining an observation regarding a substance or compound of interest (preferably an analyte), as a (in particular final) result of an assay method on a sample.

“Diagnostic method” is understood herein as a method which is carried out on a sample obtained from an animal body of a subject, preferably patient, and which comprises detection, preferably determination, assessment or a measurement of a parameter of the sample, preferably the presence or level or concentration of a substance, highly preferably an antibody, evaluation of the result of the observation or a measurement and a conclusion on the condition or status of said subject. In an embodiment said conclusion may provide a basis for decision regarding a treatment.

“Comparing” two levels, preferably levels of two compounds or two patterns of compounds, is understood herein to include a comparison of quantities expressed in numerical values characterizing said levels to establish which is higher or lower, or establishing a difference or establishing a ratio of the levels, or values derived from the levels, optionally completed with other mathematical procedures as the quantification or calculation method requires.

The terms “comprises” or “comprising” or “including” are to be construed here as having a non-exhaustive meaning and allow the addition or involvement of further features or method steps or components to anything which comprises the listed features or method steps or components.

The expression “consisting essentially of” or “comprising substantially” is to be understood as consisting of mandatory features or method steps or components listed in a list e.g. in a claim whereas allowing to contain additionally other features or method steps or components which do not materially affect the essential characteristics of the use, method, composition or other subject matter. It is to be understood that “comprises” or “comprising” or “including” can be replaced herein by “consisting essentially of” or “comprising substantially” if so required without addition of new matter.

ABBREVIATIONS aPSA antiPSA
APTS aminopyrene-1,3,6-trisulfonic acid
CE capillary electrophoresis
CDR complementary determining region
DTT dithiothreitol
GU glucose unit
LoD limit of detection
mAb monoclonal antibody
MS mass spectrometry
HR-NCHO (high resolution N-linked carbohydrate),
PCa prostate cancer
PSA prostate-specific antigen
sdAb single domain antibody
SDS sodium-dodecyl-sulphate

DETAILED DESCRIPTION OF THE INVENTION

Figure 1:
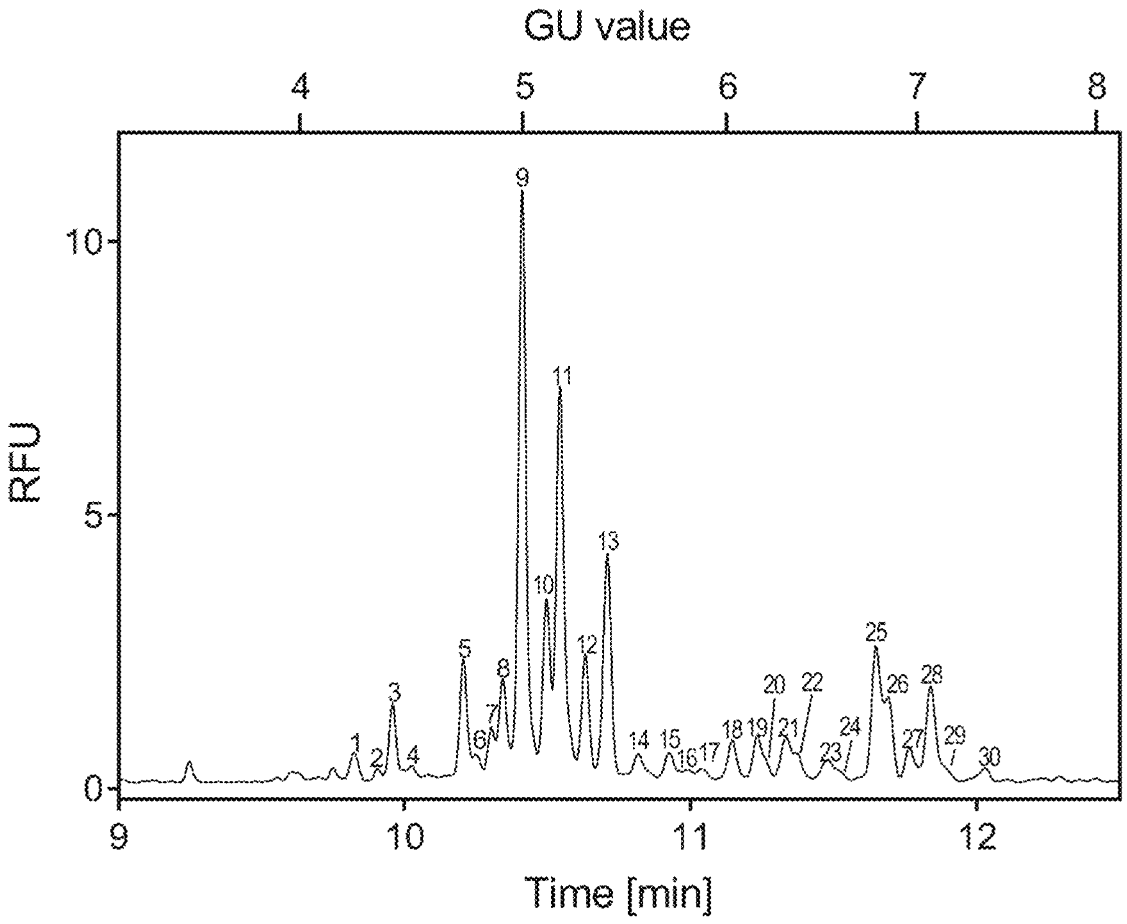
FIG. 1. Capillary electrophoresis separation of the APTS-labeled standard PSA N-glycome. Separation conditions: 50 cm total (40 cm effective) length, 50 μm i.d. bare fused silica capillary with HR-NCHO gel buffer. Voltage: 30 kV (0.5 min ramp); Temperature: 25° C.; Injection: 5 psi/5 sec water pre-injection followed by 5 kV/2 sec sample. Structures corresponding to peaks are listed in Table 1.

The present inventors have developed a high-throughput capillary electrophoresis (CE) based glycan analysis workflow capable to process and analyze urinary prostate-specific antigen (PSA). The demonstrated technology utilizes a selective, high yield single domain antibody based PSA capture followed by preconcentration and capillary electrophoresis coupled by laser-induced fluorescence detection separation steps resulting in high resolution N-glycan profiles. The patient PSA glycan profile is compared with a commercially available PSA standard revealing that the suggested methodology provides reliable data even capable to differentiate α2,3- and α2,6-sialylated isomers. The latter plays an important role in classification between indolent, significant, and aggressive forms of prostate cancer.

The novel, integrated workflow was established for urinary PSA N-glycosylation analysis utilizing highly selective sdAb-based capture from a biological matrix, high throughput preconcentration, enzymatic release of N-glycans from PSA, fluorescent carbohydrate labeling, high resolution capillary electrophoresis separation and comprehensive glycan structure elucidation.

In this invention, a new method step was introduced to isolate PSA from urine samples by an affinity purification or partitioning column comprising immobilized PSA-specific binding molecules. The skilled person is aware that several types of such binding molecules may be used. Such binding molecules may include proteins of antibody derived protein scaffolds, like antibody fragments, single-domain antibodies, single chain antibody fragments (scFv), Fab fragments, nanobodies etc. (Muyldermans, 2021).

Alternatively, a binding molecule can be entirely artificially made, e.g. as a synthetic peptide. Thus, binding molecules include proteins of non-antibody protein scaffolds like fibronectin, lipocalins, anticalins, (Škrlec et al., 2015; Stern et al., 2013; Gebauer & Skerra, 2019).

In a highly preferred embodiment immobilized antiPSA nanobodies are used. In a highly preferred embodiment such antibodies are applied on IMAC-Ni microcolumns. In the present exemplary embodiment the sdAbs were produced in-house and were engineered with a special linker tag to help their anchoring to the column matrix. The usage of sdAbs over mAbs may facilitate extension of the application in future clinical tests as their production even at larger quantities is possible with lower costs. The selective capturing procedure contributed both to remove other glycoprotein contaminants from the biological matrix and preconcentrating the PSA content, resulting in higher detection signal.

Sample concentration is an important feature of the process. In a preferred embodiment the eluted samples are concentrated. In a preferred embodiment a filter with an appropriate cut-off is used, said cut-off is preferably between 5 to 20 kDa, highly preferably about 10 kDa. In a preferred embodiment spinfilters are applied and centrifugation is used to concentrate the sample. Centrifugation may be carried out typically with 5000 to 20000 g, preferably 10000 to 15000 g, for 2 to 20 minutes, as required, preferably for 5 to 15 minutes, more preferably for 8 to 12 minutes at 10000 to 15000 g. The samples are cooled as needed, e.g. to 1 to 10° C. In a preferred embodiment the samples are dried and resolved again. The volume of the samples is preferably 1 to 20 μl, more preferably about 10 μl.

Sample preparation preferably and usually includes denaturation of the protein. The use of magnetic beads supports the removal of excess fluorescent dye from the labeling reaction mixture. The dye shall be used in a relatively large excess in the reaction. In aqueous medium the glycans are solution together with the fluorescent dye whereas in the organic phase the labeled glycans attach to the surface of the magnetic beads. As the dye does not attach to the surface of the beads it can be removed by washing.

The denaturation solution typically comprises one or more types of detergents, e.g. nonionic and/or ionic detergent(s) or mixture thereof. The ionic detergent may be anionic or cationic detergents. A typical anionic detergent comprises an alkyl-sulphate, e.g. dodecyl-sulphate. The counter ion is a positive or a negative ion, respectively. In an example the mixture may be that of a nonionic detergent, like Nonidet and of an anionic detergent like SDS.

The denaturation solution may also comprise a reducing agent to keep amino acids, like cysteine, in a reduced state. Such reducing agents may comprise DTT and/or beta-mercaptoethanol, among others.

Analysis of the oligosaccharides of PSA require a glycan derivatization step: glycans may be derivatized to introduce a chromophore or fluorophore, facilitating detection after chromatographic or electrophoretic separation. Here fluorescent labeling of glycans was applied. Today fluorescent labeling methodology can be considered as a routine for a person skilled in the art and several labeling kits are available like, merely as examples, labeling kits from Glycan labeling products from Merck like GlycoProfile™ Labeling Kit. In the examples the Fast Glycan Labeling and Analysis Kit was from SCIEX (Brea, CA, USA) including the tagging dye of 8-aminopyrene-1,3,6-trisulfonic acid (APTS).

In an example the labeling solution may comprise a mixture of the tagging dye, e.g. APTS and aqueous solvent mixture comprising an organic acid, e.g. AcOH, an organic solvent, e.g. THF, and a reducing agent, e.g. a borohydride derivative, like Sodium cyanoborohydride in an appropriate ratio.

Magnetic beads are used for removing excess dye. Magnetic bead suspension: the solvent was removed from 200 μl of magnetic bead suspension from the Fast Glycan Labeling and Analysis Kit on a magnetic stand, the beads were resuspended in 200 μl of water and the solvent was removed again on a magnetic stand, the beads were resuspended again in 20 μl of water The glycans were removed from PSA by using enzymatic removal technologies. The enzyme should be one which results in a deaminated protein or peptide and a free glycan, e.g. an enzyme which cleaves between the innermost GlcNAc and asparagine residues of a glycoprotein (e.g. PSA) and thus cleaves high mannose, hybrid, and complex oligosaccharides from N-linked glycoproteins and glycopeptides. An example is Peptide: N-glycosidase F, commonly referred to as PNGase F, an amidase of the peptide-N4-(N-acetyl-beta-glucosaminyl) asparagine amidase class.

Sequencing should also use a set of exoglycosidase enzymes, including e.g. sialidase (e.g. Sialidase A), galactosidase (e.g. β-Galactosidase), hexosaminidase (β-N-Acetyl Hexosaminidase), etc. and also an endoglycosidase (PNGase F). Upon sequencing, repeated cleavage steps are carried out in a well defined order to explore the sequence of sugar moieties in the glycan structure.

Capillary electrophoresis and methods for its application to N-glycosylation analysis of prostate-specific antigen are known in the art in general and reviewed e.g. by Reider et al. (Reider et al., 2020). The present inventors have found that while using a longer capillary the separation improves, but the method can be carried out with a relatively short capillary as well.

In a particular embodiment capillary gel electrophoresis is carried out with a capillary of at least 5 cm and at most 100 cm effective length, preferably at least 10 cm and at most 60 cm effective length, highly preferably at least 15 cm and at most 50 cm effective length. Preferably, a longer capillary of 30 to 50 cm effective length is used for standard PSA glycan analysis and sequencing and a shorter one with 10 to 30 cm effective length for captured urinary PSA glycan analysis. In a particular embodiment, a fused silica capillary is used, preferably a bare fused silica capillary.

Separation gel buffers are known in the art, in a particular solution HR-NCHO separation gel buffer (high resolution N-linked carbohydrate; SCIEX) is used.

The applied electric field is a reversed polarity field of 20 to 40 kV, preferably 25 to 35 kV, highly preferably 28 to 32 kV.

The separation temperature can be optimized, however, in a particular method it is 20-37° C., preferably 25 to 35°, highly preferably 28 to 32° C.

The CE-LIF analysis of the released glycans from urinary PSA resulted in 19 structures out of the 30 obtained from standard PSA. Each identified glycan structure originated from native PSA was sialylated, suggesting that the mild conditions of both the capture and analysis procedure preserved the labile sugar residues, e.g., sialic acids. Due to the high resolving power of CE, both the fucosylated and non-fucosylated structures as well as the α2,3- and α2,6-sialylated isomers were separated. Since the most common cancer related alterations are reportedly associated with these structures, it was key for any diagnostic application to reliably detect any possible changes in these residues. Furthermore, as not only glycan types but individual structures were identified more complex alterations could be discovered, which occurs in certain glycans only. Our results showed that the developed workflow was suitable for comprehensive N-glycan analysis of urinary PSA and could be a basis for future endeavors aiming to detect the alterations in PSA glycosylation caused by certain diseases like prostate cancer or benign prostatic hyperplasia.

Therefore, the present method is useful for obtaining a glycosylation pattern from the urine sample. A glycosylation pattern may comprise data on individual glycan structures in a sample. The data comprise values typical of the glycan structures given or selected, e.g. on the ratio or level of individual glycans in the urine PSA sample. In a preferred embodiment the pattern comprises data on at least 4, 5, 6, 7, 8, 9, 10, 11, 12, 13, 14, 15, 16, 17, 18 or 19 glycan structures from the 19 structures obtained by CE-LIF analysis of the present inventors.

Typical values which can be used to obtain a glycosylation pattern may include but not limited to the presence, any typical ratio or level, e.g. concentration, percentage, composition of one or more selected glycans. The pattern necessarily comprises structure information on the glycans, e.g. comprise also the sequence of the glycans.

Thus, the glycosylation pattern may comprise data on multiple glycan structures. Preferably it comprises data regarding at least fucosylated and non-fucosylated structures. Moreover it also comprises data regarding at least the α2,3- and α2,6-sialylated isomers. Moreover it also comprises data regarding both.

By analyzing samples of healthy subjects (or patients) a normal glycosylation pattern can be established.

Preferably the glycosylation pattern data comprise ranges for each glycan. In case of a normal glycosylation pattern each range indicates the values (e.g. ratio or level) typical of the corresponding glycan which indicates the normal range. In case of a healthy subject (or patients) the values or at least the values for the majority of the glycans, preferably at least 80%, or 90% or 95% of the glycans fall into the normal range.

Quite similarly glycosylation pattern typical for various PSA-related conditions can be obtained by analyzing, using the method of the invention, samples of patients having the specific PSA-related condition. Such can be e.g. benign prostatic hyperplasia, prostate cancer including a metastatic cancer, or a precancerous condition e.g. a condition that is likely to progress to cancer.

Thereby a set of reference glycosylation pattern can be established.

In a diagnostic method the glycosylation pattern obtained by analyzing a patient sample can be compared with a typical glycosylation pattern, e.g. a glycosylation pattern typical of a PSA-related condition or a normal glycosylation pattern.

Comparing glycosylation patterns can include comparing any data determined by the methods of the present invention, including but not limited to the presence, concentration, percentage, composition or sequence of one or more selected glycans of the target glycoprotein, to the reference. This comparison allows diagnosis, staging, prognosis or monitoring of the PSA-related condition.

The invention also allows providing a database comprising a plurality of records.

The database, or e.g. the records, preferably each record can include the data as described above.

More specifically the database may comprise:

reference glycosylation patterns, like normal glycosylation pattern and optionally one or more glycosylation patterns typical of a PSA-related condition.

In an embodiment records of the database may comprise one or more of the following:

- data on the glycosylation pattern of PSA associated with a disorder isolated from a sample from a subject obtained by determining the glycosylation profile of said subject by the method of the present invention; and optionally
- data on the status of the subject, e.g., whether the subject has cancer, a pre-cancerous condition, a benign condition, or no condition, and any clinical outcome data, e.g., metastasis, recurrence, remission, recovery, or death;
- data on any treatment administered to the subject;
- data on the subject's response to treatment, e.g., the efficacy of the treatment; personal data on the subject, e.g., age, gender, education, etc. and/or environmental data, such as the presence of a substance in the environment, residence in a preselected geographic area, and performing a preselected occupation. In some embodiments, the database is created by entering data resulting from determining the glycoprofile of a target glycoprotein in a sample from a subject using a method described herein.

The diagnostic method of the invention preferably comprises

- determining a glycosylation pattern according to the invention in the sample of a patient (patient glycosylation pattern),
- comparing the glycosylation pattern with a normal glycosylation pattern, and
- if there is a difference between the patient glycosylation pattern and the normal glycosylation pattern the patient is considered as having a PSA-related condition.

In a further embodiment, the diagnostic method of the invention preferably comprises

- determining a glycosylation pattern according to the invention in the sample of a patient (patient glycosylation pattern),
- comparing the glycosylation pattern with a reference glycosylation pattern typical of a PSA-related condition, and if
- the patient glycosylation pattern is identical with a reference glycosylation pattern the patient is diagnosed as having the PSA-related condition.

In general, the method of the invention comprises detecting alterations in the PSA-glycosylation pattern.

In an embodiment the invention comprises detecting alterations in the sialylation of the glycan moieties.

In an embodiment the invention comprises detecting alterations in the fucosylation of the glycan moieties.

In preferred embodiments of the invention the method comprises detecting alterations in both the sialylation and fucosylation patterns.

In preferred embodiments of the invention the method comprises a fingerprint analysis of the PSA-glycosylation pattern.

In a preferred embodiment the invention also relates to methods of determining whether a subject has prostate cancer, comprising determining whether a subject has an altered PSA alpha-2,3-sialylation pattern as compared to the alpha-2,3-sialylation pattern of PSA from a healthy subject, wherein an altered PSA alpha-2,3-sialylation pattern is indicative of prostate cancer.

In a preferred embodiment the method of the invention comprises measuring whether the level of alpha-2,3-sialylated glycans or the ratio of the level of alpha-2,3-sialylated glycans and a reference value (level or ratio for alpha-2,3-sialylated glycans, respectively) is/are increased as compared to a normal level or ratio typical of a healthy subject. The reference value can be a value or range, e.g. an amount or level calculated from the total amount or level of glycans or the amount or level of a given number of predetermined glycans, i.e. a set of glycans or a specific glycan. Alternatively, the reference can be the PSA-level or the level of another protein, e.g. a household protein. In a particular method a ratio of the level of alpha-2,3-sialylated glycans and a reference value is formed. In an embodiment the level of alpha-2,3-sialylated glycans is measured and compared to a normal value. The normal value can be a value or range, e.g. an amount or level calculated from a set of measurements for samples of healthy subjects by the assay method of the invention.

In a preferred embodiment if the level or the ratio for alpha-2,3-sialylated glycans is above a threshold level the subject is diagnosed as having prostate cancer or showing tendency for prostate cancer if the ratio is higher than a threshold value.

In a particular embodiment the present invention relates to a method for diagnosis of a subject for prostate cancer comprising determining the ratio of the amount of glycan in which the terminal sialic acid residue of the glycan is ±(2,3)-linked to a second galactose residue from the terminal of the glycan, to a reference value and the subject is diagnosed as having prostate cancer or showing tendency for prostate cancer if the ratio is higher than a threshold value.

In a preferred embodiment the invention also relates to methods of determining whether a subject has prostate cancer, comprising determining whether a subject has an altered PSA alpha-2,6-sialylation pattern as compared to the alpha-2,6-sialylation pattern of PSA from a healthy subject, wherein an altered PSA alpha-2,6-sialylation pattern is indicative of prostate cancer.

In a preferred embodiment the method of the invention comprises measuring whether the level of alpha-2,6-sialylated glycans or the ratio of the level of alpha-2,6-sialylated glycans to alpha-2,3-sialylated glycans and a reference value (level of alpha-2,6-sialylated glycans or ratio of alpha-2,6-sialylated glycans to alpha-2,3-sialylated glycans, respectively) is/are increased as compared to a normal level or ratio typical of a healthy subject. The reference value can be a value or range, e.g. an amount or level calculated from the total amount or level of glycans or the amount or level of a given number of predetermined glycans, i.e. a set of glycans or a specific glycan. In a particular method a ratio of the level of alpha-2,6-sialylated glycans to alpha-2,3-sialylated glycans and a reference value is formed. In an embodiment the level of alpha-2,6-sialylated glycans is measured and compared to a normal value. The normal value can be a value or range, e.g. an amount or level calculated from a set of measurements for samples of healthy subjects by the assay method of the invention.

In a preferred embodiment if the level or the ratio of alpha-2,6-sialylated glycans to alpha-2,3-sialylated glycans is above a threshold level, the subject is diagnosed as having prostate cancer or showing tendency for prostate cancer.

In a preferred embodiment the invention also relates to methods of determining whether a subject has prostate cancer, comprising determining whether a subject has an altered PSA fucosylation pattern as compared to the fucosylation pattern of PSA from a healthy subject wherein an altered PSA fucosylation pattern is indicative of prostate cancer.

In a preferred embodiment the method of the invention comprises measuring whether the level of fucosylation or the ratio of the level of fucosylated glycans and a reference value (level or ratio for fucosylated glycans, respectively) is/are increased as compared to a normal level or ratio typical of a healthy subject. The reference value can be a value or range, e.g. an amount or level calculated from the total amount or level of glycans or the amount or level of a given number of predetermined glycans, i.e. a set of glycans or a specific glycan. Alternatively, the reference can be the PSA-level or the level of another protein, e.g. a household protein. In a particular method a ratio of the level of fucosylated glycans and a reference value is formed. In an embodiment the level of fucosylated glycans is measured and compared to a normal value. The normal value can be a value or range, e.g. an amount or level calculated from a set of measurements for samples of healthy subjects by the assay method of the invention.

In a preferred embodiment if the level or the ratio for fucosylated glycans is above a threshold level the subject is diagnosed as having prostate cancer or showing tendency for prostate cancer.

Below the invention is illustrated further by way of Examples which are, however, non-limiting and provide description of particular embodiments for illustrative purposes.

EXAMPLES

Materials and Methods

Chemicals and Reagents

Water (HPLC grade), acetic acid (glacial), acetonitrile (MeCN), sodium cyanoborohydride (1 M in THF), sodium chloride, imidazole, 4-(2-hydroxyethyl)-1-piperazineethanesulfonic acid (HEPES) and DTT (dithiothreitol) were obtained from Sigma Aldrich (St. Louis, MO, USA). SDS (sodium dodecyl sulfate) and Nonidet P-40 were from VWR (West Chester, PA, USA). The Fast Glycan Labeling and Analysis Kit was from SCIEX (Brea, CA, USA) including the tagging dye of 8-aminopyrene-1,3,6-trisulfonic acid (APTS), magnetic beads for excess dye removal, HR-NCHO separation gel-buffer system, the bracketing standards of maltose (DP2) and maltopentadecaose (DP15). The exoglycosidase enzymes of Sialidase A (*Arthrobacter ureafaciens*), β-Galactosidase (Jack bean) and β-N-Acetyl Hexosaminidase (Jack bean) were from ProZyme (Hayward, CA, USA). The endoglycosidase PNGase F was from Asparia Glycomics, (San Sebastian, Spain). 20 ml volume 10 kDa cut-off spinfilters were from Pall (New York, NY, USA), 500 μl ml volume 10 kDa cut-off spinfilters were from VWR. PhyTip Ni-IMAC microcolumns (40 μl) were provided by PhyNexus (San Jose, CA). Buffer 'A': 100 mM HEPES, 500 mM NaCl, 50 mM imidazole, pH=8.0. Buffer 'B': 100 mM HEPES, 500 mM NaCl, 500 mM imidazole, pH=8.0. Denaturation solution: mixture of Nonidet P-40: DTT: SDS=6:1:1. Digestion solution: 75 punit/μl of PNGase F in 16.7 mM ammonium acetate. Labeling solution: 5.7 mM of APTS in the mixture of $H_2O$:AcOH:THF:$NaBH_3CN$ (1 M in THF)=5:5:8:2. Magnetic bead solution: the solvent was removed from 200 μl of magnetic bead suspension from Fast Glycan Labeling and Analysis Kit on a magnetic stand, the beads were resuspended in 200 μl of water and the solvent was removed again on a magnetic stand, the beads were resuspended again in 20 μl of water.

Gene Construction

Two antiPSA (aPSA) coding polypeptide sequences, N7 and C9 were taken from (Sacrens et al., 2004), back translated and codon optimized for *E. coli* and the genes with flanking 5'-NdeI and 3'-XhoI cleavage sites were synthetized by Genscript (Piscataway, New Jersey, United States). After amplification both genes were cloned into pET23b (Novagen, Merck, Darmstadt, Germany) between its NdeI and XhoI sites, thus fusing a C-terminal 6-histidine coding sequence to the gene of aPSA. Proper incorporation of the insert into the plasmid was verified by sequencing (Macrogen Europe B.V., Amsterdam, the Netherlands).

Protein Expression and Purification

For protein expression Shuffle T7 Express *E. coli* (New England Biolabs, Ipswich, Massachusetts, US) cells were transformed with the N7-aPSA-pET23b and C9-aPSA-pET23b plasmids, according to the supplier's protocol. 5 mL sterile Luria Broth (LB) media containing 100 μg/mL Ampicillin (Amp) was inoculated from a freshly prepared LB/Amp plate and grown at 30° C. with vigorous shaking until OD600 was between 0.4-0.6 and kept at 4° C. overnight. The cells were then separated from the supernatant by centrifugation, resuspended in 5 mL freshly prepared LB and 2 mL of it was used to inoculate 1 L LB/Amp. Cell culture was grown at 37° C. for two hours and then at 30°, 140 rpm in baffled flask until OD600 fell into 0.6-1 and then the temperature was decreased down to 22° C. After 15 min of cooling protein expression was induced by the addition of 0.5 mM isopropyl β-D-1-thiogalactopyranoside (IPTG, final concentration) and further incubated overnight. Cells were harvested by centrifugation at 6,000 g for 30 min, washed with buffer 'A' and centrifuged again at 10,000 g for 30 min. Cells were resuspended again on ice in 20 ml buffer 'A' containing two EDTA-free Mini Complete protease inhibitor tablets (Roche, Basel, Switzerland) and disrupted by sonication (10×30 s, 50% amplitude). The suspension was centrifuged at 30,000 g and the supernatant filtered through a 0.45 μm syringe filter. Sample was loaded on a pre-equilibrated 5 ml HiTrap Chelating (GE Healthcare, Chicago, Illinois, US) nickel saturated column and purified using isocratic elution and the pure protein was eluted at 50% 'B' buffer. In order to get rid of the high salt and imidazole content of the protein solution, it was dialyzed against a buffer solution. Purity of aPSA was confirmed on 15% SDS PAGE gels and protein concentration calculated using the following parameters given by ProtParam (Gasteiger et al., 2005): N7-aPSA-6His, 14.5 kDa, 27,180 $cm^{-1}M^{-1}$ and C9-aPSA-6His, 14.3 kDa, 21,555 $cm^{-1}M^{-1}$, respectively.

Biological Specimens

Urine samples were collected with the appropriate Ethical Permissions (approval number: 23580-1/2015/EKU (0180/15)) and Informed Patient Consents in the Semmelweis Hospital (Miskolc, Hungary). Samples were taken from male and female (blind control) healthy volunteers (population of seven Caucasian, age average: 28.3, age median 27) and kept at 4° C. until processing.

PSA Quantitation in Urine

All standard ELISA tests were carried using a UniCel DxI 800 Access Immunoassay System, kindly provided by the central laboratory of Csolnoky Ferenc Hospital (Veszprem, Hungary). Urine samples were analyzed directly, without any sample preparation.

PSA Capture from Urine 300 ml of male urine was cooled to room temperature and it was concentrated to 500 μl by 20 ml volume 10 kDa cut-off spinfilters (13,500 g for 30 min at 6° C. for each consecutive 20 ml concentration). The concentrated urine was diluted and centrifuged (13,500 g for 10 min at 6° C.) twice with 3-3 ml of buffer 'A' then it was transferred to an Eppendorf vial. The filter was washed two times with 250 μl buffer 'A' each and both were added to the transferred urine. The final, 1 ml mixture was vortexed and divided into two 500-500 μl, one for PSA capture and one for control. Two Ni-IMAC microcolumns were washed by 200 μl buffer 'A' for 5 min, by connecting the tips to an automated pipette and the buffer was continuously aspirated and dispensed through the tips with the flow rate of 2 ml/min. In the next step, the tips were washed by 50 μg/ml C9 sdAb in 100 μl buffer 'A' for 10 min. For control sample 100 μl buffer 'A' without sdAb was used instead. Both of the tips were washed again by 200 μl buffer 'A' for 5 min. Then, the tips were washed by 500-500 μl concentrated urine samples for 10 min. After that, the tips were washed again 3 times with 200 μl of buffer 'A', 5 min each, then washed by 100 μl buffer 'B' for 5 min. The eluted buffers (containing the targets) were transferred onto 500 μl volume 10 kDa cut-off spinfilters and the solvent was centrifuged (13,500 g for 10 min at 6° C.). The filter was washed twice by 400 μl of water, both times the water was centrifuged (13,500 g for 10 min at 6° C.). The samples were taken up into 80 μl water (washing the filter twice with 40-40 μl of water), transferred into an Eppendorf vial, then they were dried in a SpeedVac under reduced pressure at 70° C. for 15 min. The dried sample was resolved again in 10 μl of water.

Sample Preparation

The sample preparation process was identical for all captured PSA, control and standard PSA (150 μg/ml) samples. 2 μl of denaturation solution was added to 10 μl sample, and it was heated up from 30° C. to 80° C. in 8 min 20 sec and was incubated at 80° C. for 1 min 40 sec. Then 20 μl of digestion solution was added and the sample was heated up from 40° C. to 60° C. in 20 min. After that, labeling solution was added and sample was incubated at 37° C. overnight in an open cap vial to let the solvent evaporate. The dried sample was then resolved in 20 μl of magnetic bead solution, then 185 μl of MeCN was added and solvent was removed from the magnetic beads on a magnetic stand. The beads were suspended in 20 μl of water, 185 μl of MeCN was added and the solvent was removed from the magnetic beads on a magnetic stand again. This step was repeated two additional times (total of 4 washes with the first one adding the beads). Finally, beads were diluted with 60 μl of water and, on a magnetic stand, 50 μl of sample was transferred into a new vial to CE analysis.

Glycan Structure Identification

Structural elucidation of separated, asparagine linked PSA glycans was utilized by direct mining of GU database entries (GUcal.hu), exoglycosidase digestion based carbohydrate sequencing and some earlier published literature data on the same subject matter (Kammeijer et al., 2018; Mészáros et al., 2020). Exoglycosidase sequencing was utilized in an automated fashion as reported in Szigeti & Guttman, 2017. Shortly, the released N-glycans were consequently digested by monomer and anomericity specific exoglycosidase enzymes such as Sialidase A, β-Galactosidase and β-N-Acetyl Hexosaminidase. Native, i.e., undigested and all digested pools were then separated by CE-LIF and the structural information was derived from the GU value shifts of the individual peaks as the result of the consecutive exoglycosidase treatments (Guttman & Ulfelder, 1997).

Capillary Gel Electrophoresis

A PA800 Plus Pharmaceutical Analysis System (SCIEX) with laser induced fluorescence detection (λex=488 nm/λem=520 nm) was used for all capillary gel electrophoresis separations employing the HR-NCHO separation gel buffer in a 40 cm effective length (50 cm total length, 50 μm ID) bare fused silica capillary for standard PSA and sequencing, and 20 cm effective length (30 cm total length, 50 μm ID) bare fused silica capillary for captured urinary PSA. The applied electric field strength was 30 kV in reversed polarity mode (cathode at the injection side, anode at the detection side). The separation temperature was set at 30° C. A three-step electrokinetic sample injection was applied: 1) 3.0 psi for 5.0 sec water pre-injection, 2) 1.0 kV for 1.0 sec sample injection and 3) 1.0 kV for 1.0 sec bracketing standard (BST, DP2 and DP15). The 32Karat (version 10.1) software package (SCIEX) was used for data acquisition and interpretation.

Results

Identification of Standard PSA Glycosylate

Figure 2:
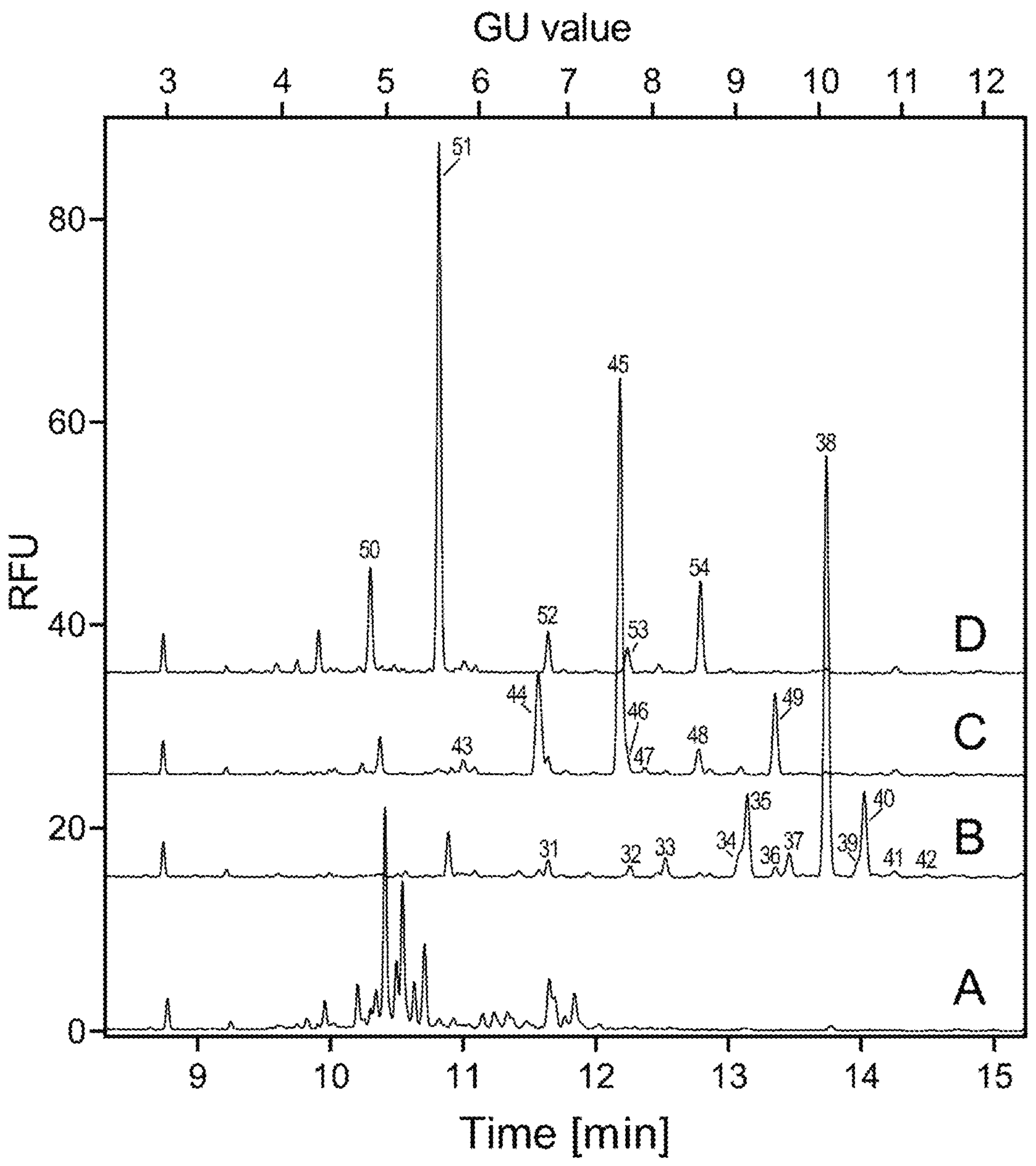
FIG. 2. Exoglycosidase based sequencing of standard PSA N-glycome. Standard PSA (A), after Sialidase A digestion (B), after Sialidase A, β-Galactosidase digestion (C), after Sialidase A, β-Galactosidase and β-N-Acetyl Hexosaminidase digestion (D). Separation conditions were the same as in FIG. 1. Structures corresponding to peaks are listed in Table 1.

The global N-glycosylation profile of standard PSA was analyzed in order to establish a reference point for the workflow development process. 40 cm effective length capillary was utilized to achieve high resolution glycan profile as depicted in FIG. 1, wherein the 30 most relevant peaks are annotated. The name, structure, migration time and GU values of all identified glycans are listed in Table 1. The exoglycosidase based glycan sequencing process is shown in FIG. 2, utilizing Sialidase A, β-Galactosidase and β-N-Acetyl Hexosaminidase, depicted by the corresponding traces. Sequence information was derived from the GU value shifts of the individual peaks as the result of the consecutive exoglycosidase treatments in (Szigeti & Guttman, 2017). As one can observe, all of the identified structures on the standard PSA sample were sialylated, emphasizing the surprising advantage of CE-LIF as a gentle separation technique being able to preserve sensitive glycan isomers. Orthogonal techniques, like MS often leads to de-sialylation due to in-source degradation (Kammeijer et al., 2017). Furthermore, the high resolution of CE-LIF was capable to readily differentiate the α2,3- and α2,6-sialylated isomers on mono- or multi-sialylated structures, which could be key for cancer diagnosis. Other PCa related alterations, like the degree of core fucosylation or branching could also be traceable, especially after exoglycosidase sequencing. Both, the number of identified glycans as well as the high resolution separation with reliably trackable ratios of the given structures proved the high potential of this workflow as a possible PCa diagnostic tool.

TABLE 1

Identified glycan structures from native PSA and glycan sequencing.

Figure 6:
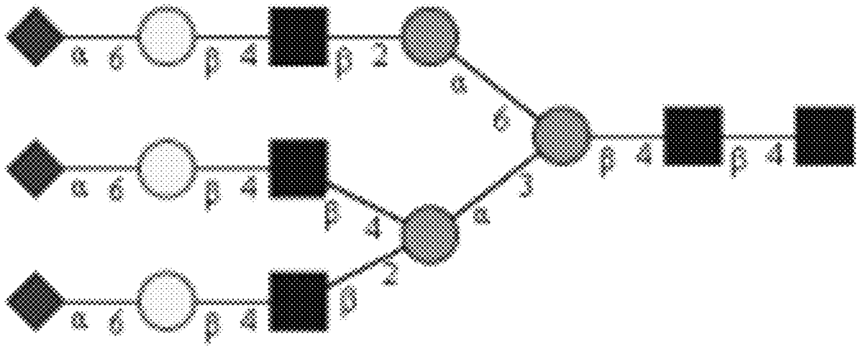
FIGS. 6-59: Identified glycan structures from native PSA and glycan sequencing.
Figure 7:
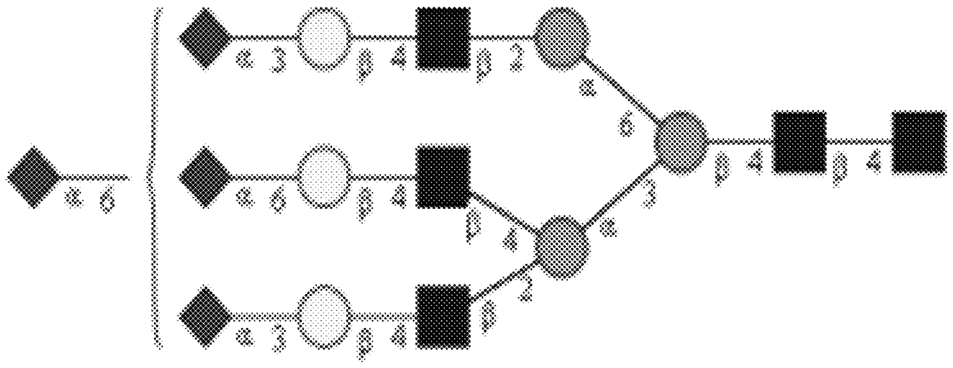
Figure 8:
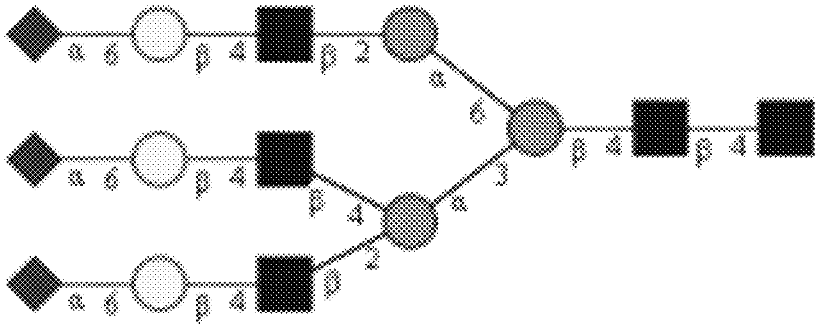
Figure 9:
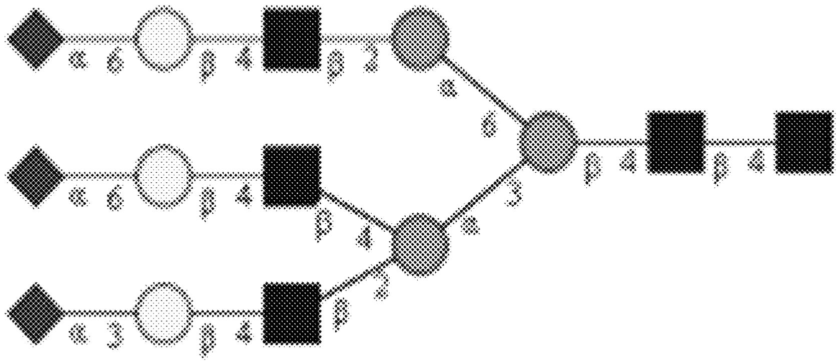
Figure 10:
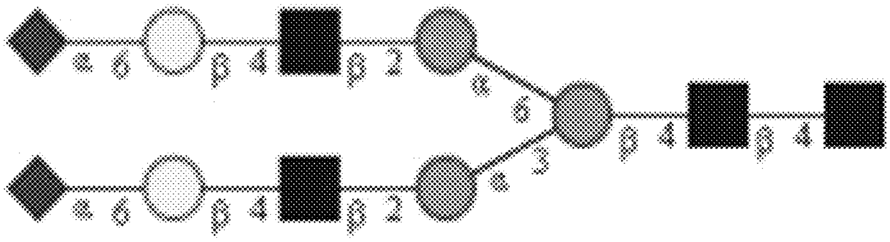
Figure 11:
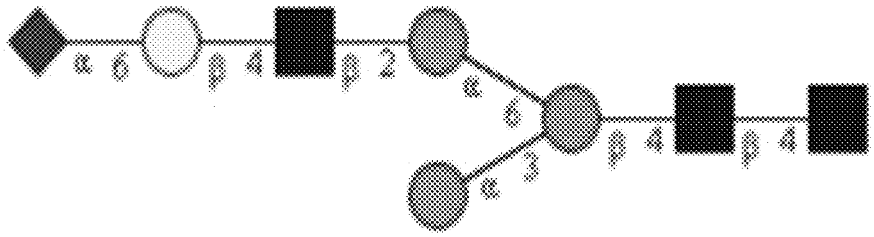
Figure 12:
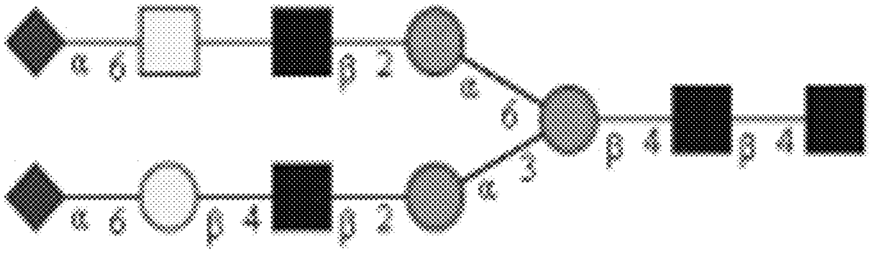
Figure 13:
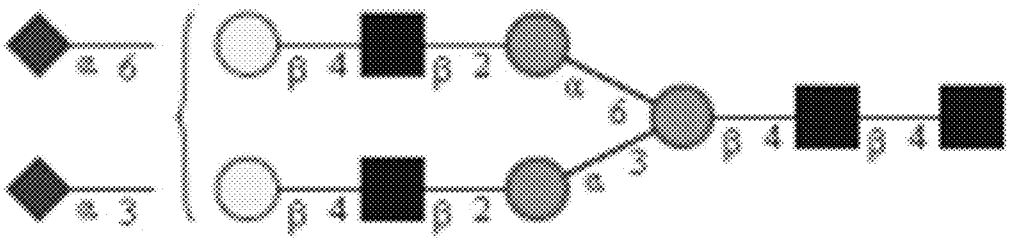
Figure 14:
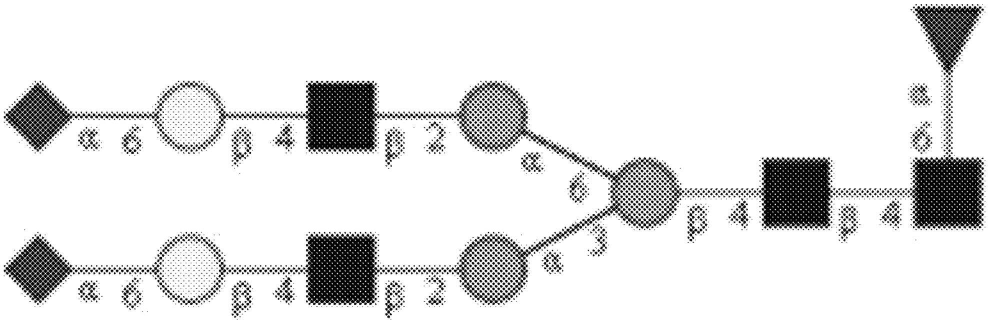
Figure 15:
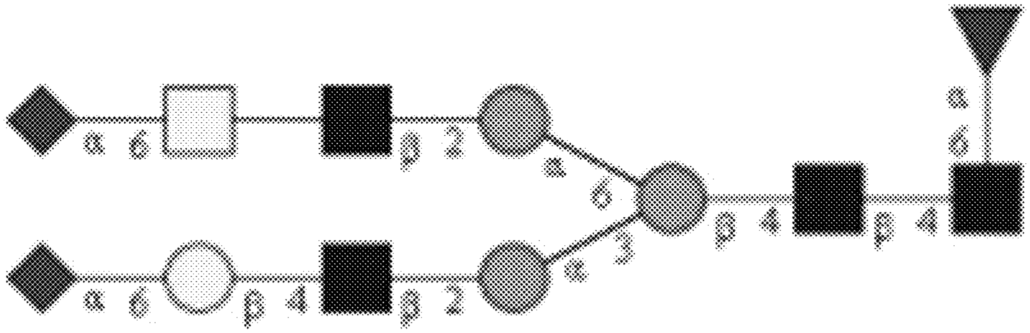
Figure 16:
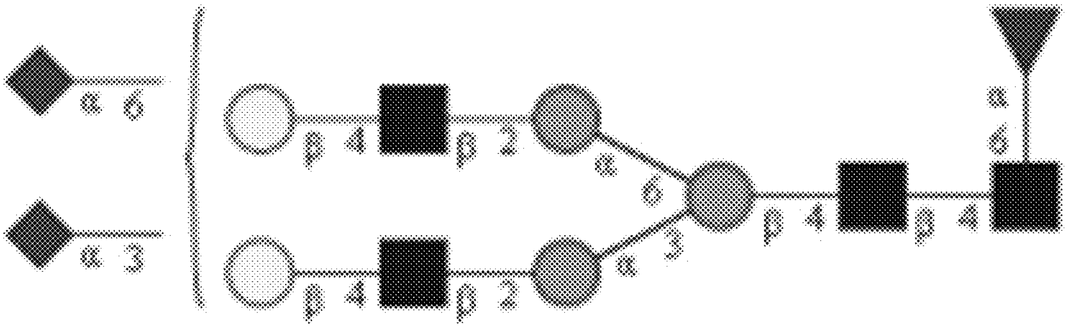
Figure 17:
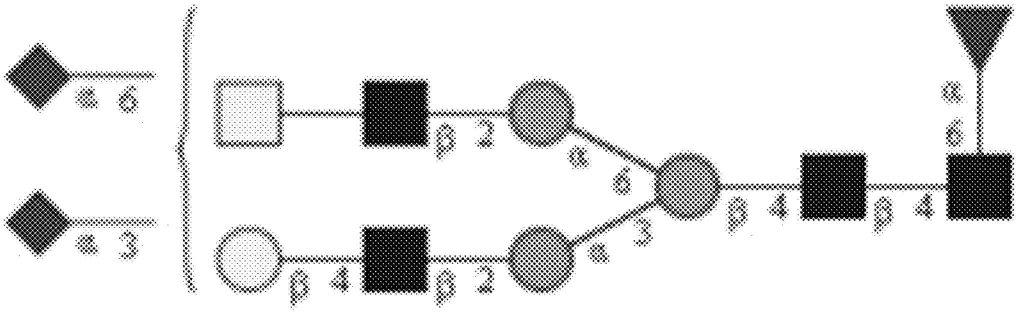
Figure 18:
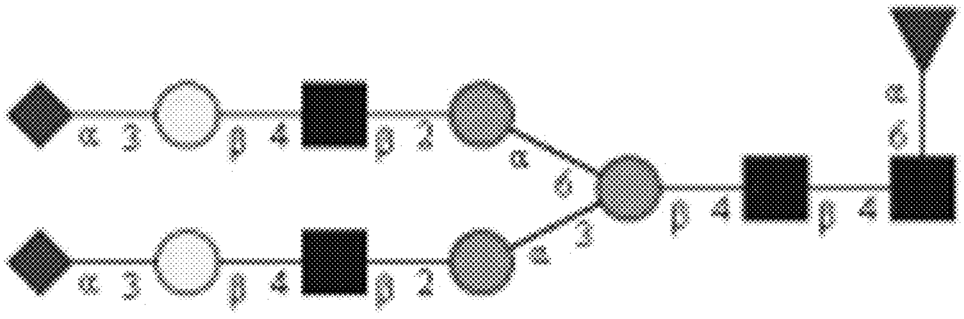
Figure 19:
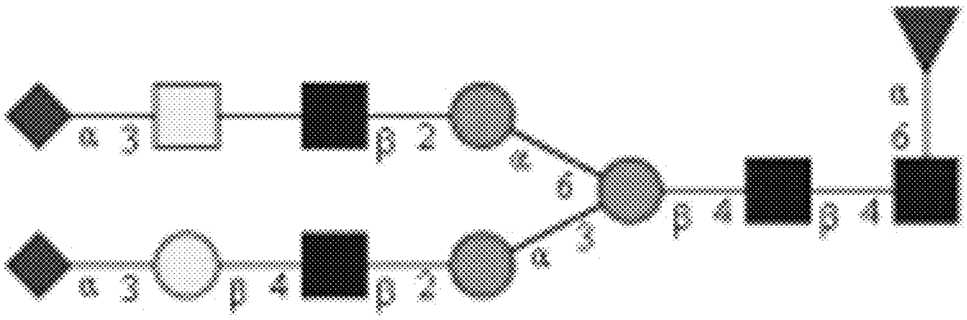
Figure 20:
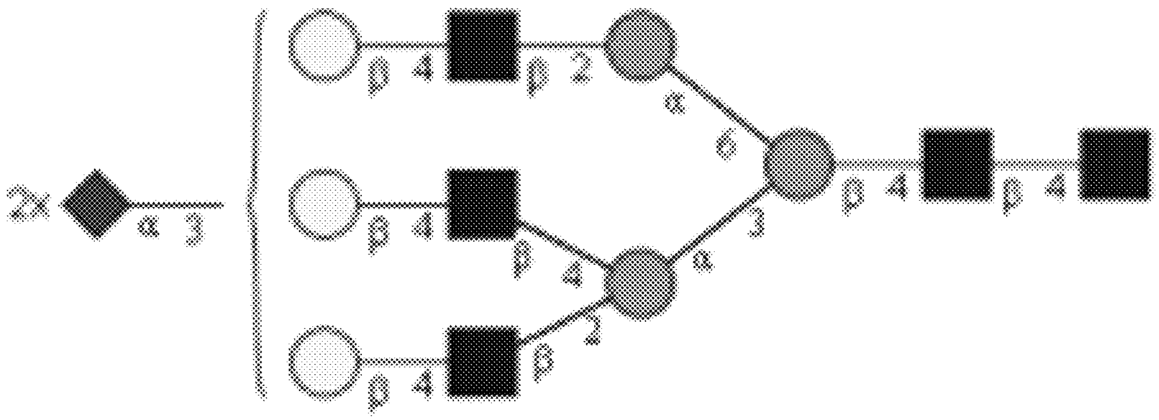
Figure 21:
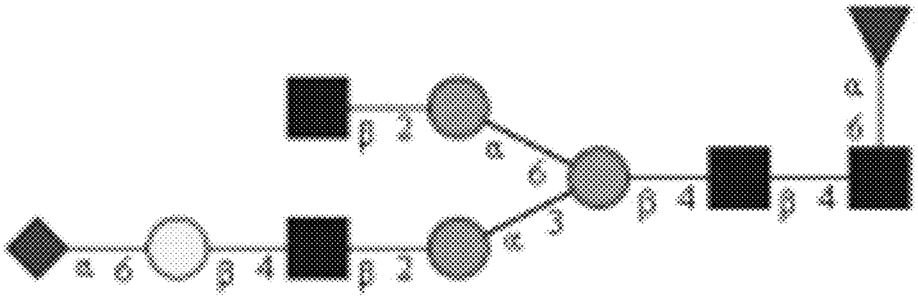
Figure 22:
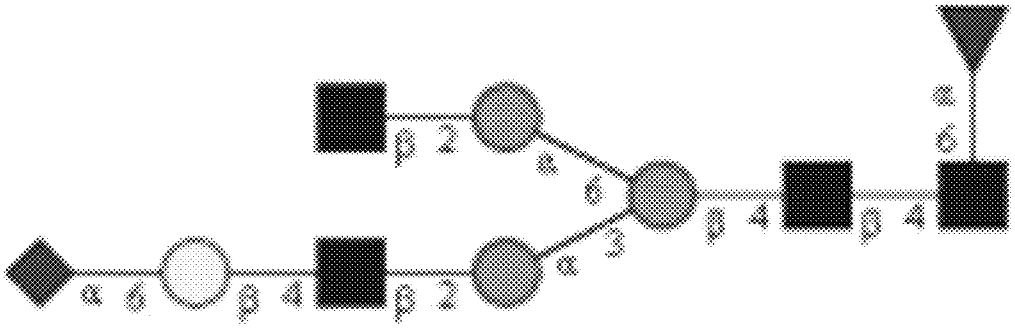
Figure 23:
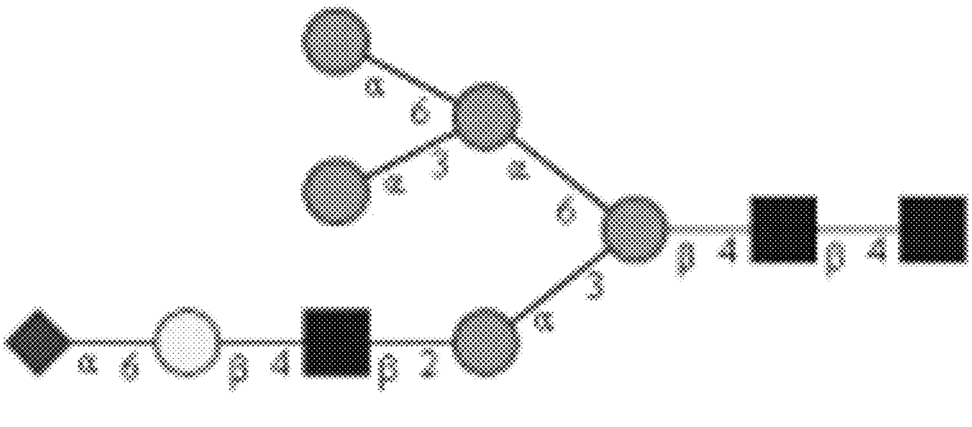
Figure 24:
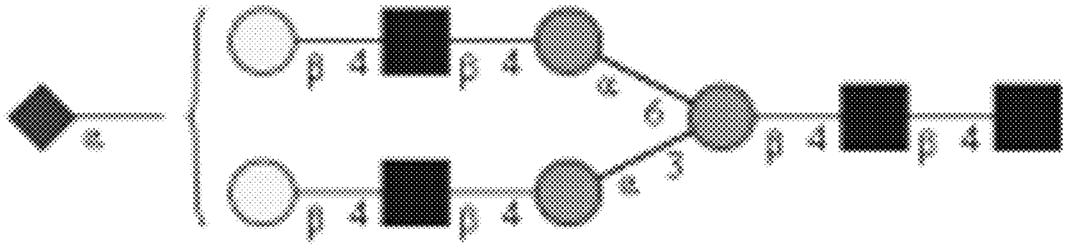
Figure 25:
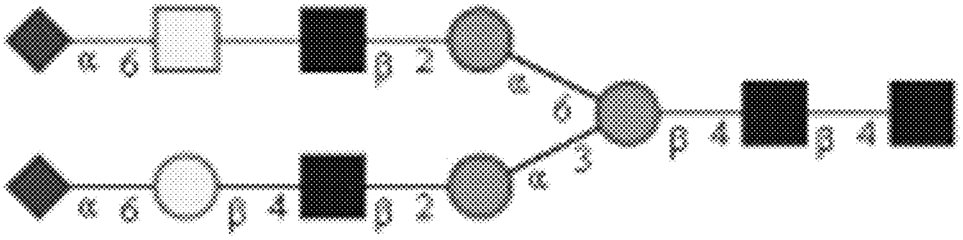
Figure 26:
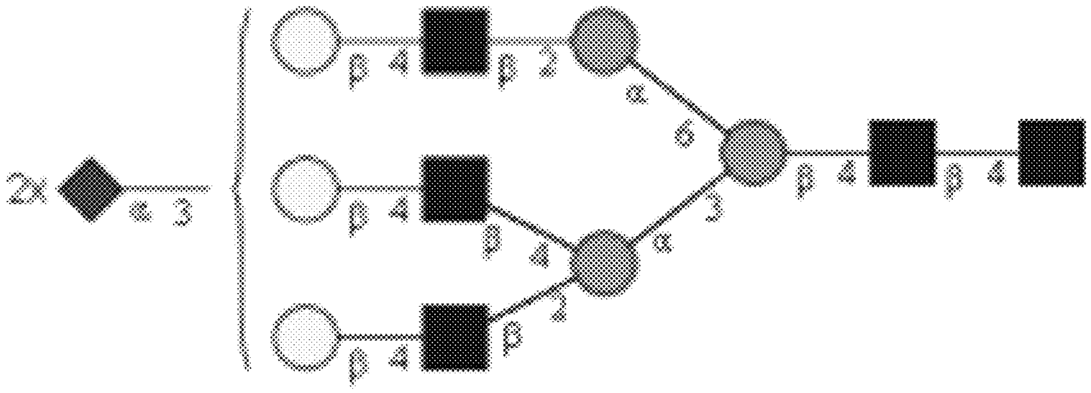
Figure 27:
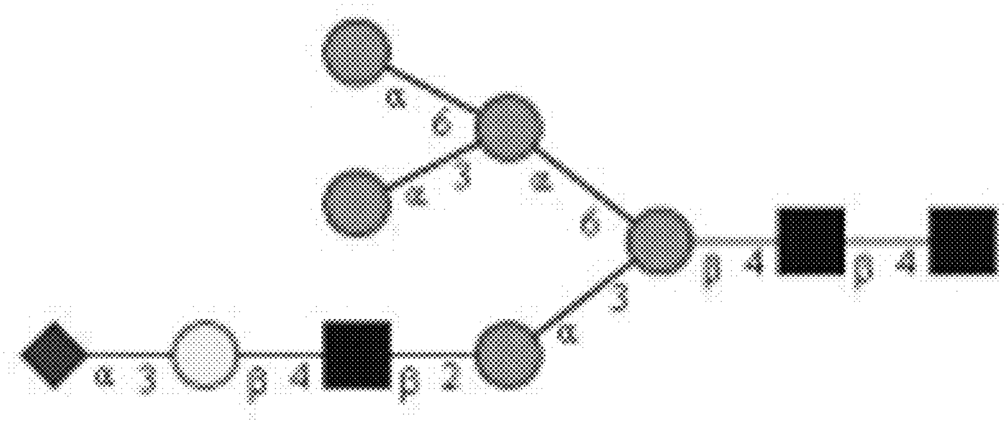
Figure 28:
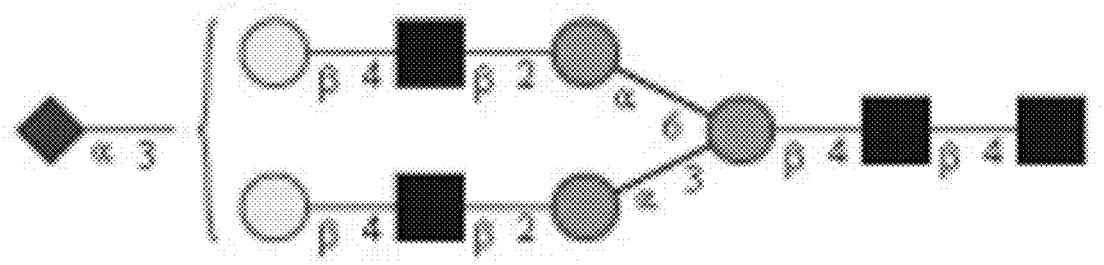
Figure 29:
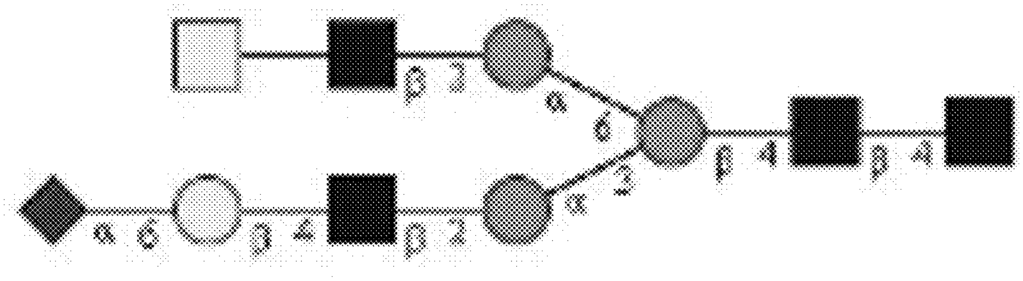
Figure 30:
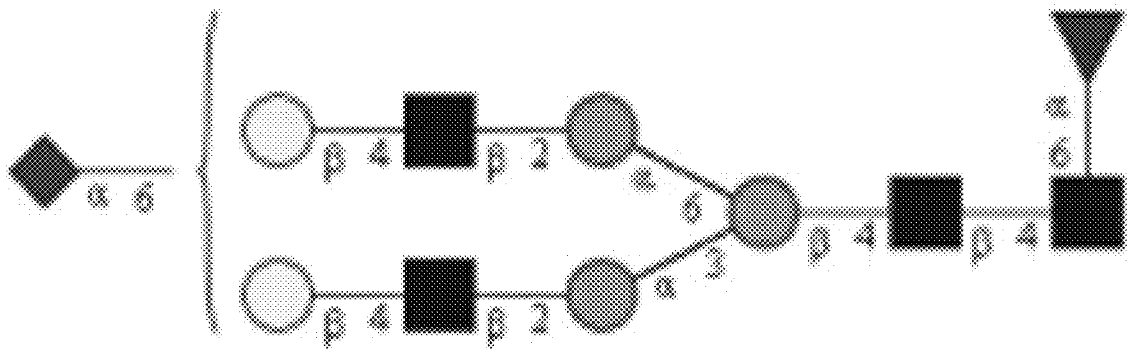
Figure 31:
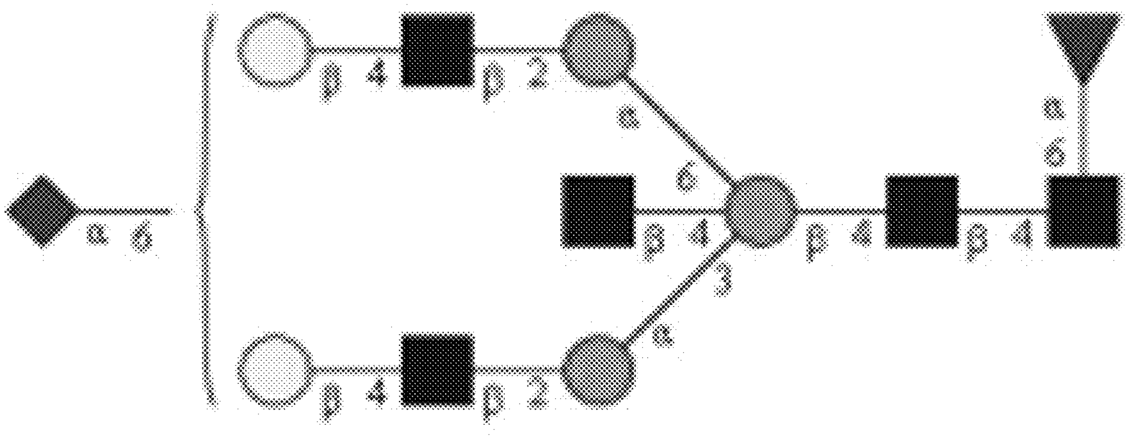
Figure 32:
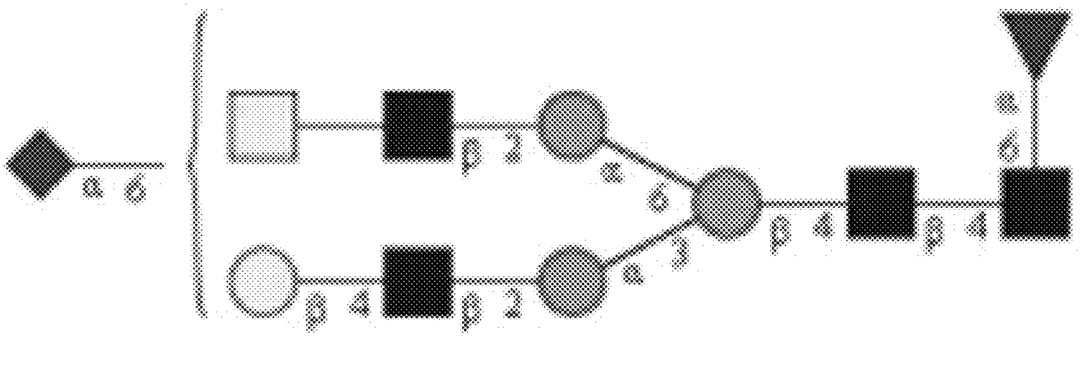
Figure 33:
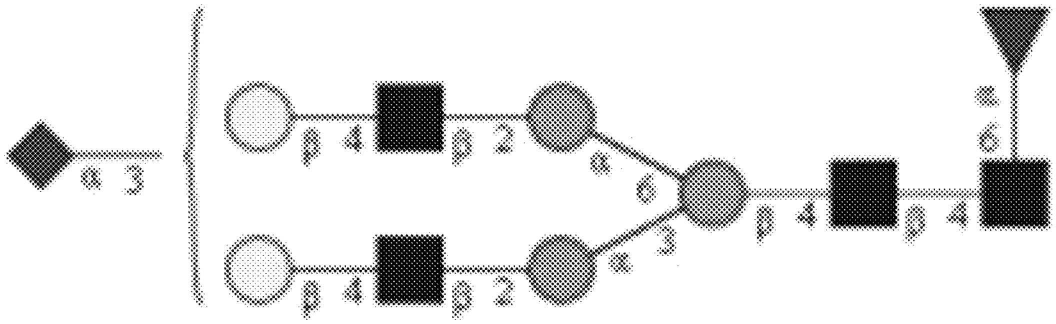
Figure 34:
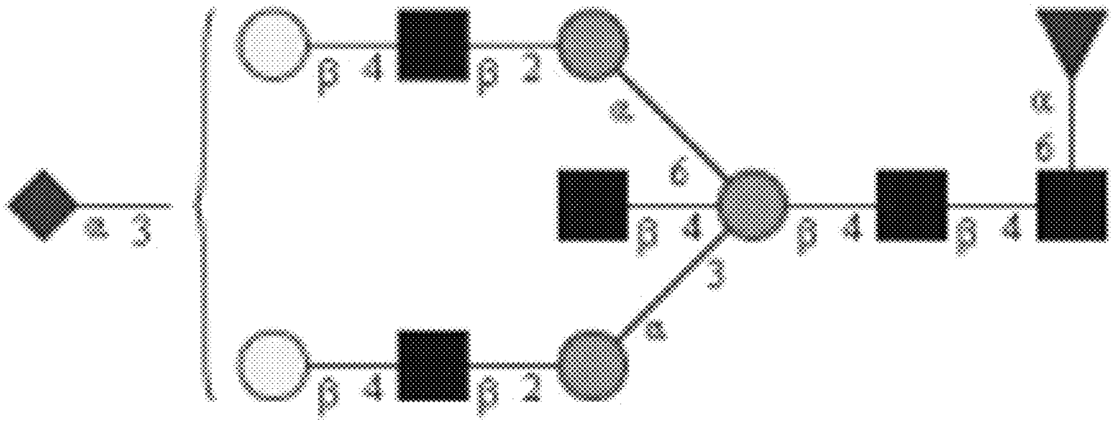
Figure 35:
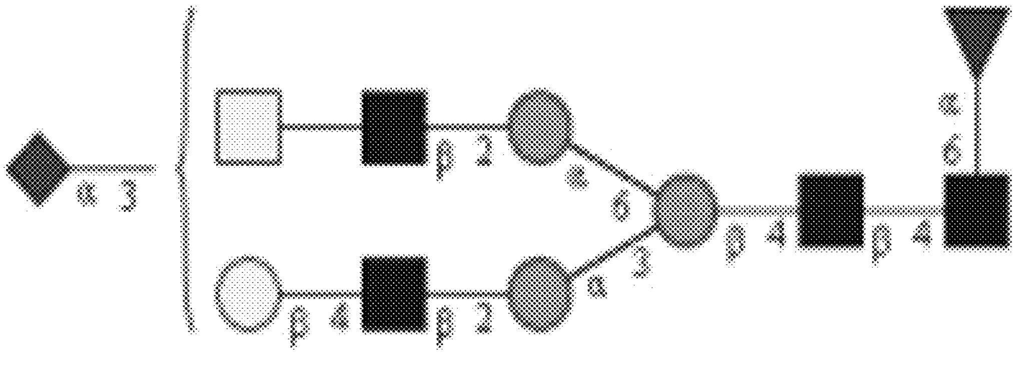
Figure 36:
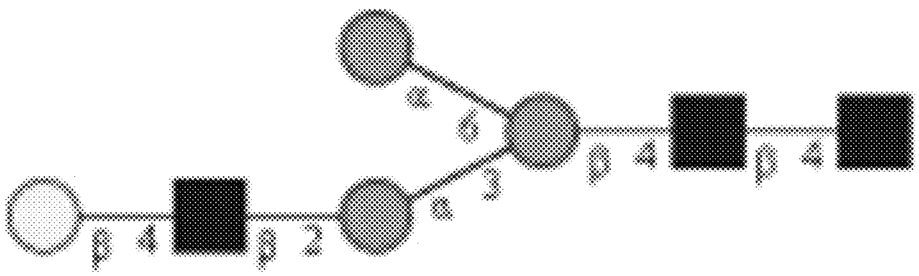
Figure 37:
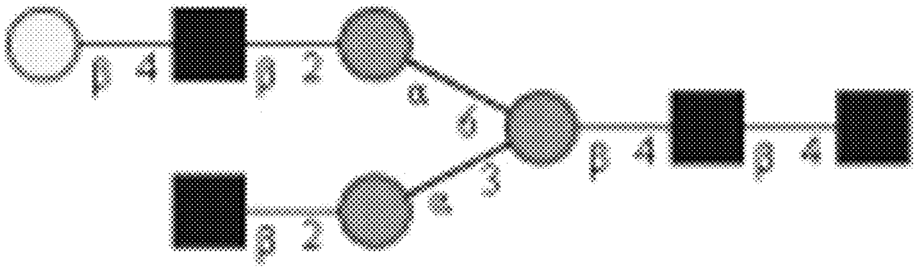
Figure 38:
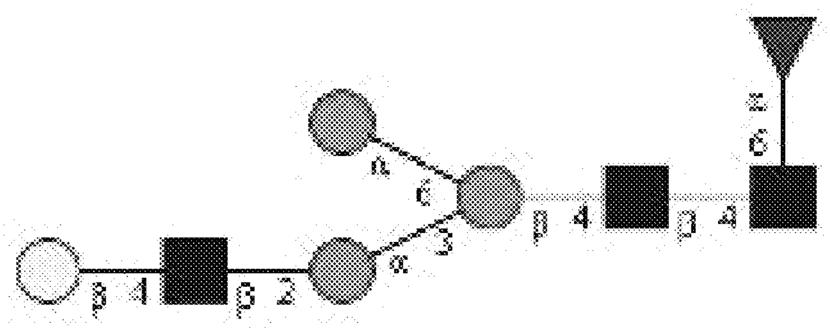
Figure 39:
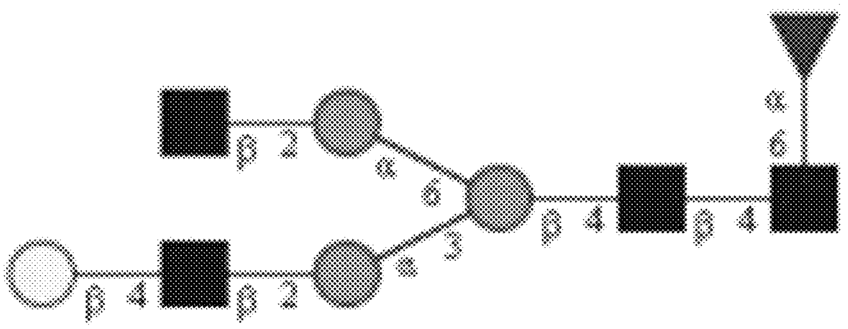
Figure 40:
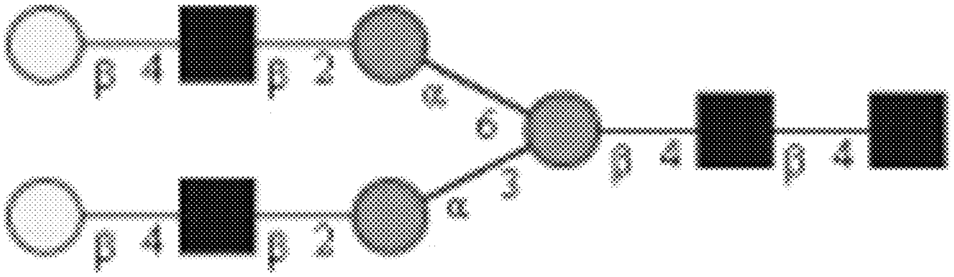
Figure 41:
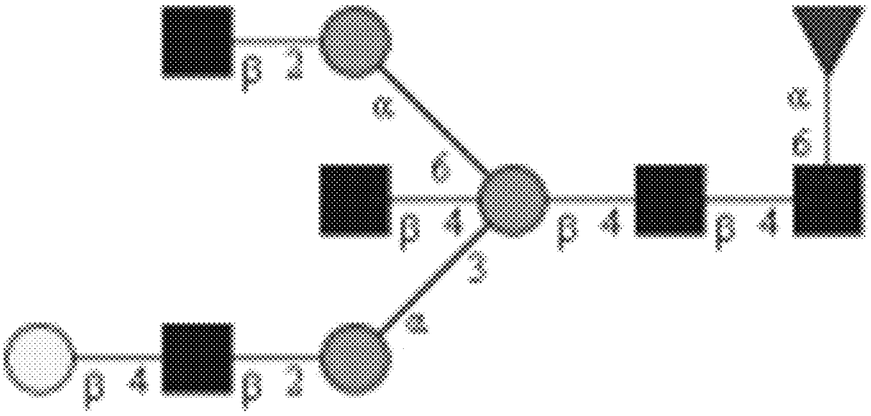

| Glycan origin | Peak No. | $t_M$ (min) | GU | Glycan name | Glycan structure formula |
|---|---|---|---|---|---|
| Native PSA | 1 | 9.82 | 4.24 | A3G(4)3S(6,6,3,6)4 | FIG. 6 |
| Native PSA | 2 | 9.91 | 4.35 | A3G(4)3S(3,6,3,6)4 | FIG. 7 |
| | 3 | 9.96 | 4.41 | A3G3(6,6,6)S3 | FIG. 8 |
| | 4 | 10.03 | 4.51 | A3G3(6,6,3)S3 | FIG. 9 |
| | 5 | 10.21 | 4.73 | A2G2(6,6)S2 | FIG. 10 |
| | 6 | 10.25 | 4.79 | A1[6]G(4)1(6)S1 | FIG. 11 |
| | 7 | 10.30 | 4.85 | A2G1NAG[6]1(6,6)S2 | FIG. 12 |
| Native PSA | 8 | 10.34 | 4.90 | A2G2(3,6)S2 | FIG. 13 |
| | 9 | 10.41 | 4.99 | F(6)A2G2(6,6)S2 | FIG. 14 |
| | 10 | 10.50 | 5.11 | F(6)A2G1NAG[6]1(6,6)S2 | FIG. 15 |
| | 11 | 10.54 | 5.18 | F(6)A2G2(3,6)S2 | FIG. 16 |
| | 12 | 10.63 | 5.30 | F(6)A2G1NAG[6]1(3,6)S2 | FIG. 17 |
| | 13 | 10.71 | 5.41 | F(6)A2G2(3,3)S2 | FIG. 18 |
| | 14 | 10.82 | 5.56 | F(6)A2G1NAG[6]1(3,3)S2 | FIG. 19 |
| Native PSA | 15 | 10.92 | 5.71 | A3G3(6,6)S2 | FIG. 20 |
| | 16 | 10.99 | 5.80 | F(6)A2[6]G(4)1(6)S1 | FIG. 21 |
| | 17 | 11.04 | 5.87 | F(6)A2[3]G(4)1(6)S1 | FIG. 22 |
| | 18 | 11.15 | 6.03 | M5A1G1(6)S1 | FIG. 23 |
| | 19 | 11.23 | 6.16 | A2G2(6)S1 | FIG. 24 |
| | 20 | 11.27 | 6.21 | A2G1NAG1(6)S1 | FIG. 25 |
| Native PSA | 21 | 11.33 | 6.31 | A3G3(3,3)S2 | FIG. 26 |
| | 22 | 11.37 | 6.36 | M5A1G1(3)S1 | FIG. 27 |
| | 23 | 11.48 | 6.53 | A2G2(3)S1 | FIG. 28 |
| | 24 | 11.53 | 6.60 | A2G1NAG1(3)S1 | FIG. 29 |
| | 25 | 11.65 | 6.78 | F(6)A2G2(6)S1 | FIG. 30 |
| | 26 | 11.69 | 6.85 | F(6)A2BG2S(6)1 | FIG. 31 |
| | 27 | 11.76 | 6.96 | F(6)A2G1NAG1(6)S1 | FIG. 32 |
| Native PSA | 28 | 11.84 | 7.08 | F(6)A2G2(3)S1 | FIG. 33 |
| | 29 | 11.89 | 7.16 | F(6)A2BG2S(3)1 | FIG. 34 |
| | 30 | 12.04 | 7.39 | F(6)A2G1NAG1(3)S1 | FIG. 35 |
| Sequencing | 31 | 11.67 | 6.82 | A1G1 | FIG. 36 |
| | 32 | 12.29 | 7.79 | A2[6]G1 | FIG. 37 |
| | 33 | 12.56 | 8.22 | F(6)A1[3]G1 | FIG. 38 |
| Sequencing | 34 | 13.12 | 9.11 | F(6)A2[3]G1 + M5A1G1 | FIG. 39 |
| | 35 | 13.17 | 9.20 | A2G2 | FIG. 40 |
| | 36 | 13.39 | 9.54 | F(6)A2BG1 | FIG. 41 |

TABLE 1-continued

Figure 42:
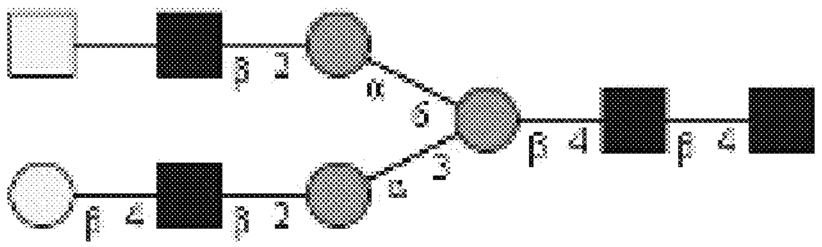
Figure 43:
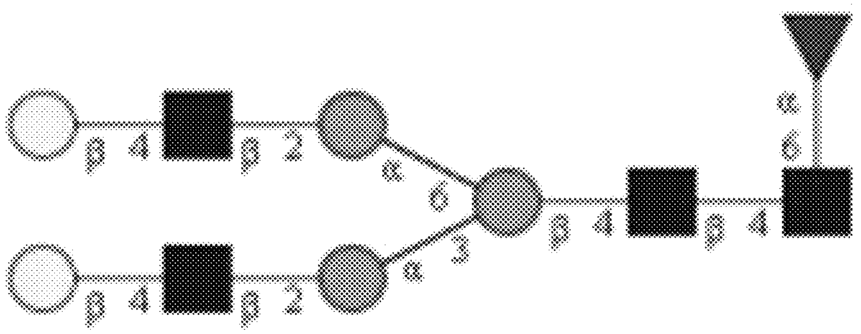
Figure 44:
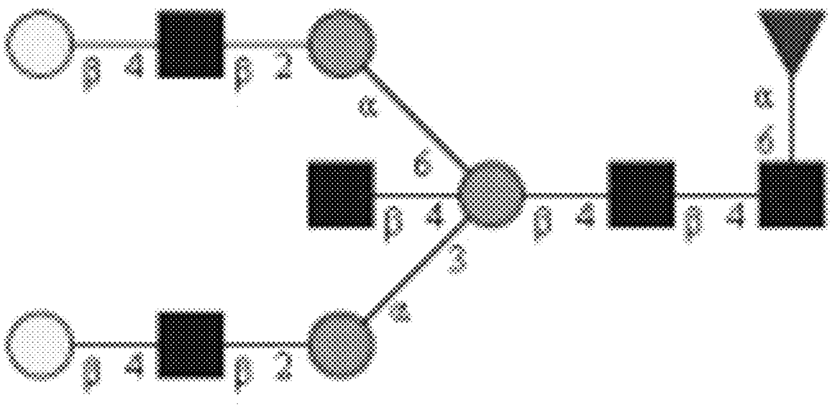
Figure 45:
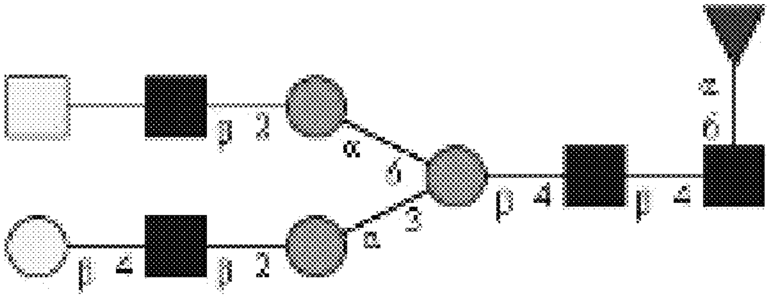
Figure 46:
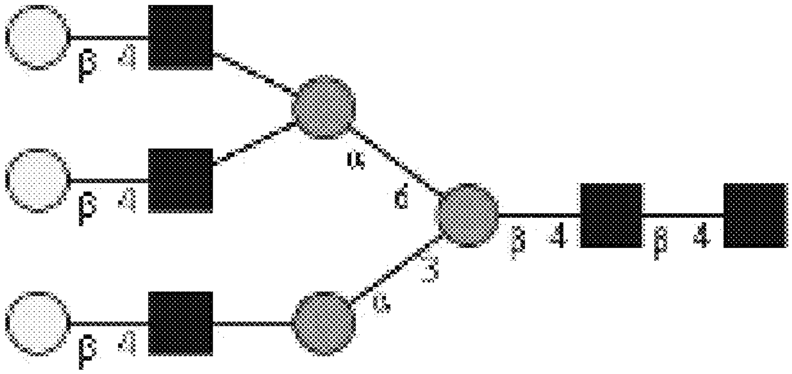
Figure 47:
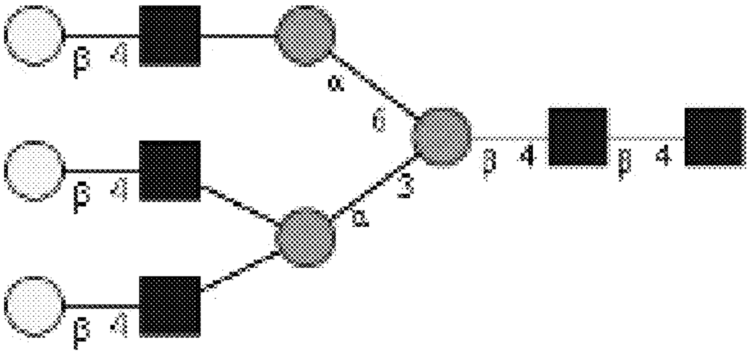
Figure 48:
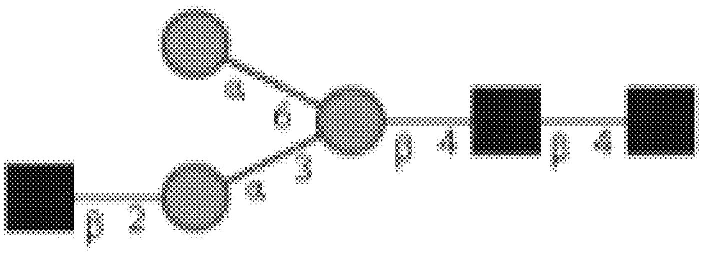
Figure 49:
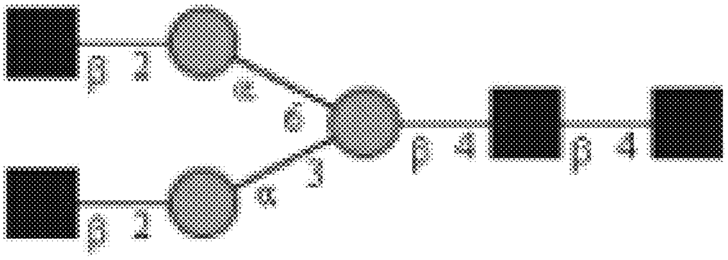
Figure 50:
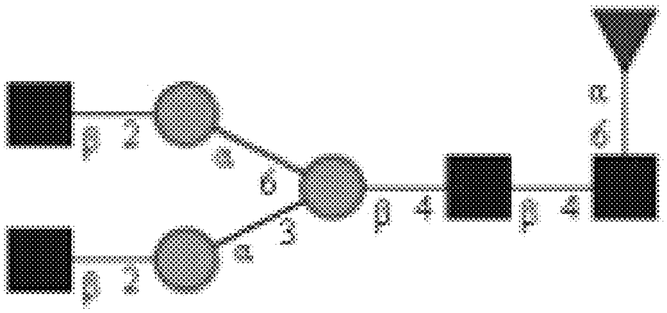
Figure 51:
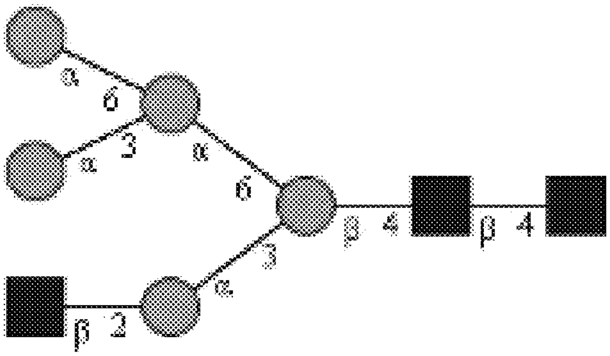
Figure 52:
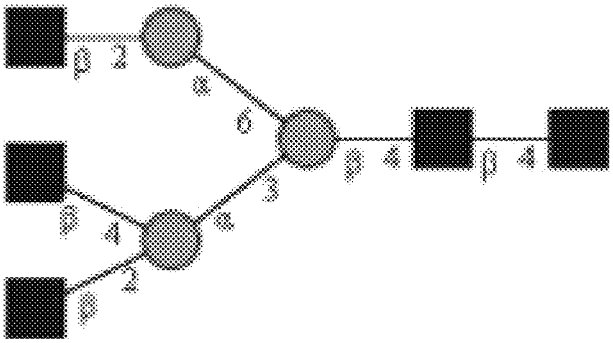
Figure 53:
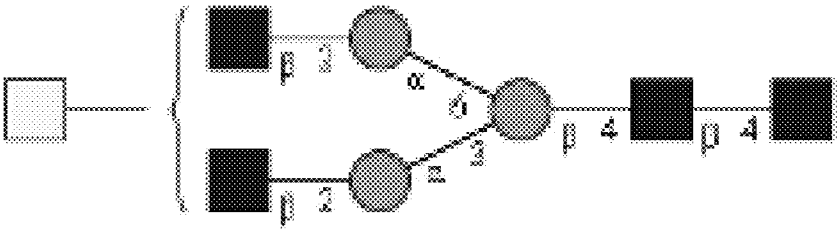
Figure 54:
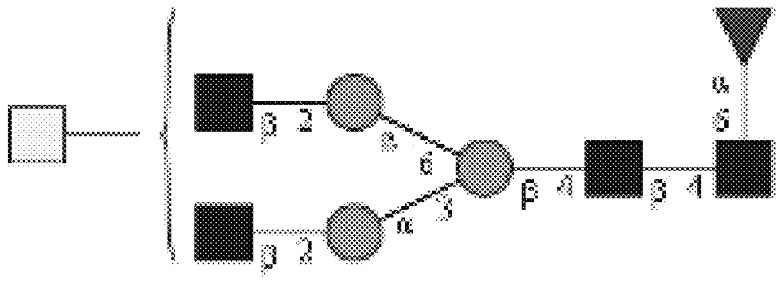
Figure 55:
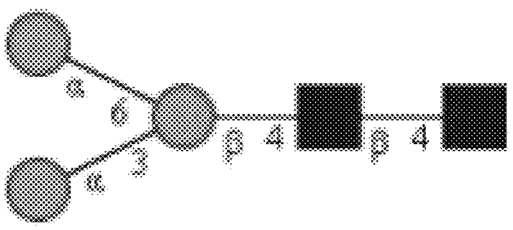
Figure 56:
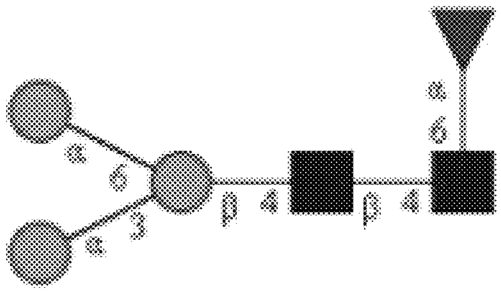
Figure 57:
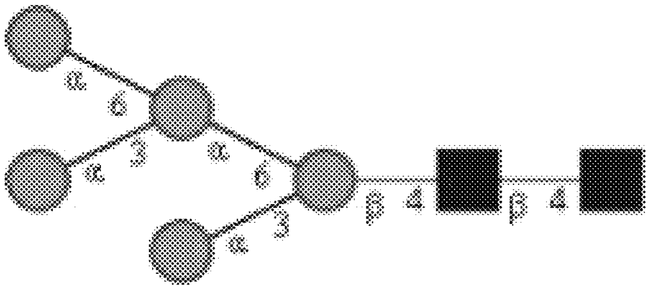
Figure 58:
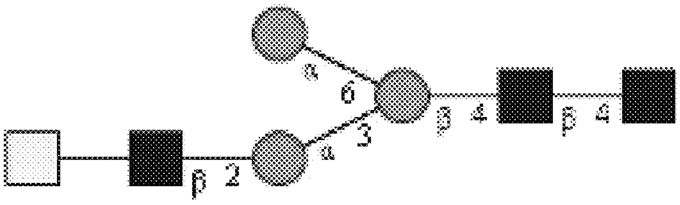
Figure 59:
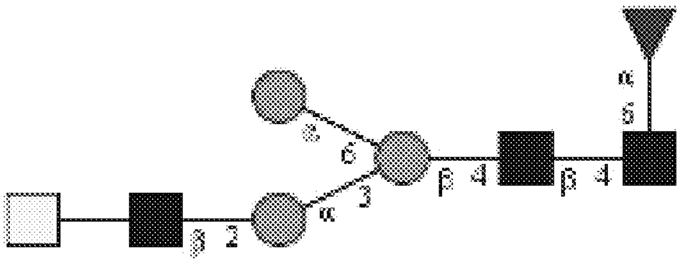

| Identified glycan structures from native PSA and glycan sequencing. | | | | | |
|---|---|---|---|---|---|
| Glycan origin | Peak No. | $t_M$ (min) | GU | Glycan name | Glycan structure formula |
| | 37 | 13.49 | 9.70 | A2G1NAG1 | FIG. 42 |
| | 38 | 13.77 | 10.14 | F(6)A2G2 | FIG. 43 |
| | 39 | 14.01 | 10.52 | F(6)A2BG2 | FIG. 44 |
| Sequencing | 40 | 14.06 | 10.60 | F(6)A2G1NAG1 | FIG. 45 |
| | 41 | 14.28 | 10.96 | A3[6]G3 | FIG. 46 |
| | 42 | 14.52 | 11.35 | A3[3]G3 | FIG. 47 |
| | 43 | 11.02 | 5.86 | A1 | FIG. 48 |
| | 44 | 11.60 | 6.72 | A2 | FIG. 49 |
| Sequencing | 45 | 12.21 | 7.67 | F(6)A2 | FIG. 50 |
| | 46 | 12.27 | 7.77 | M5A1 | FIG. 51 |
| | 47 | 12.40 | 7.97 | A3 | FIG. 52 |
| | 48 | 12.80 | 8.61 | A2NAG1 | FIG. 53 |
| | 49 | 13.38 | 9.53 | F(6)A2NAG1 | FIG. 54 |
| Sequencing | 50 | 10.33 | 4.89 | M3 | FIG. 55 |
| | 51 | 10.84 | 5.60 | F(6)M3 | FIG. 56 |
| | 52 | 11.66 | 6.81 | M5 | FIG. 57 |
| | 53 | 12.26 | 7.75 | A1NAG1 | FIG. 58 |
| | 54 | 12.81 | 8.63 | F(6)A1NAG1 | FIG. 59 |

The number of the formula is identical with the Peak No; $t_M$ is migration time.

Expression and Purification of the aPSA Proteins

Figure 3:
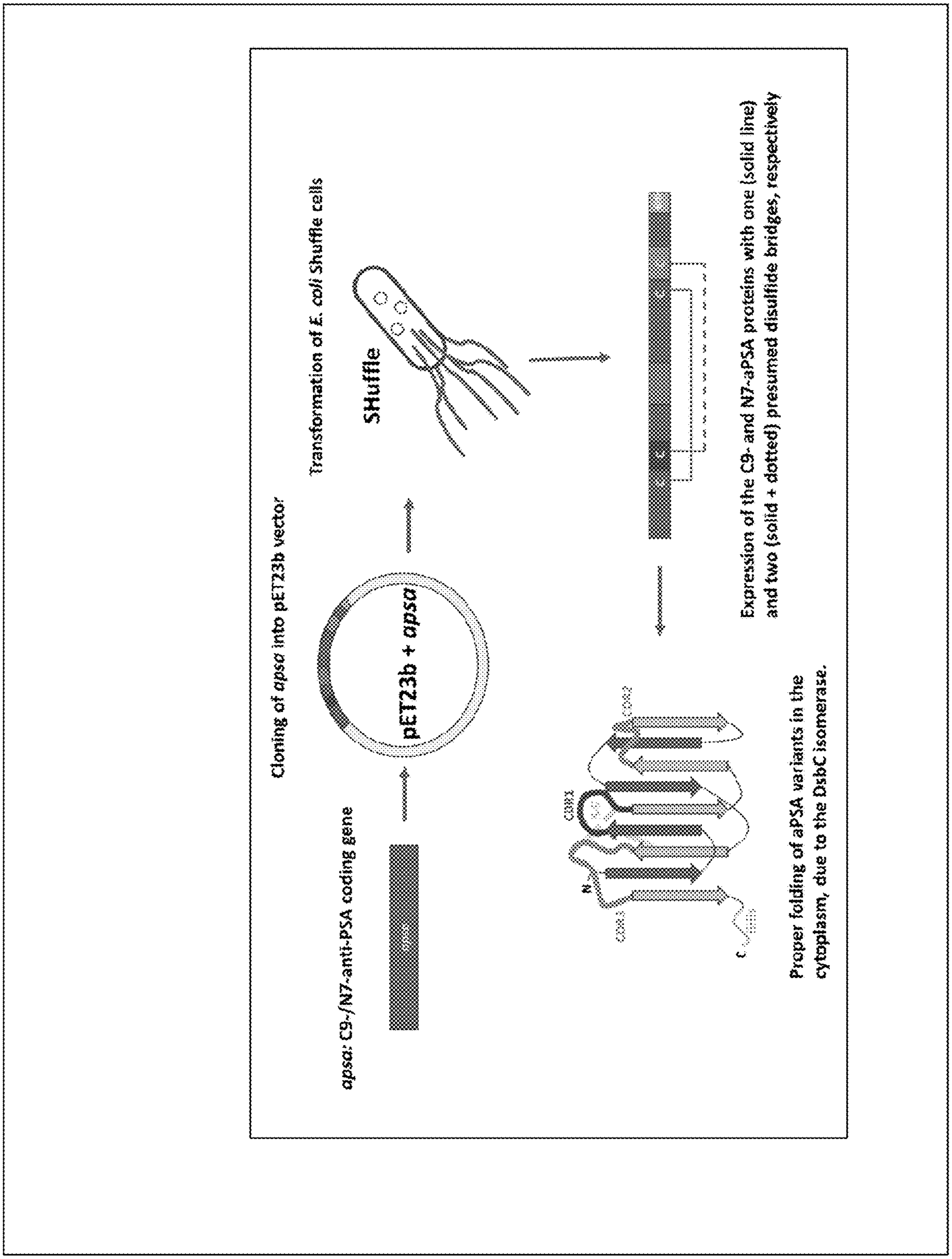
FIG. 3. Schematic of the single domain anti-PSA production. Genes of strong PSA binder N7 and C9 SdAb aPSA variants were incorporated into the pET23b expression vector and the proteins produced in SHuffle T7 Express *E. coli* cells. SHuffle ensured the proper formation of disulfide bonds, thus appropriate folding of aPSA, resulting in soluble and functional antibody for selective capture of PSA from body fluids.

Several aPSA single domain antibody sequences were selected earlier by phage display using a variant library prepared from the variable domain of the heavy-chain antibody of dromedary immunized with PSA (Saerens et al., 2004). In order to be able to collect PSA from low concentration body fluids, we chose the two strongest PSA binder variants, namely N7 ($K_d$=0.16 nM) and C9 ($K_d$=4.7 nM) (FIG. 3). The sdAbs were expressed with fused histidine tags to facilitate easy immobilization for affinity based PSA capture from urine.

C9 and N7 aPSA variants contain 2 and 4 cysteines, respectively, which make proper protein folding less effective in the cytoplasm of standard *E. coli* strains (i.e. BL21 DE3 and its derivatives). Additionally, two cysteines from the N7 variant are located in the variable regions and supposedly form a stabilizing disulfide bond on the surface of the molecule. Periplasmic expression, which had been applied also for different aPSA variants (Saerens et al., 2004), while supporting disulfide bond formation, usually results in lower protein yields. For this reason, we decided to use Shuffle T7 Express cells for protein expression, which was an engineered *E. coli* B strain capable to promote disulfide bond formation in the cytoplasm. These cells can express the disufide bond isomerase DsbC, which promoted the correction of mis-oxidized proteins into their correct form (Bessette et al., 1999; Levy et al., 2001). As a result of applying our optimized production protocol, typical yield for the aPSA variants was 8-12 mg/L culture.

PSA Capturing Procedure

Preliminary experiment suggested that the limit of detection (LoD) was approximately 500 ng of standard PSA in 10 μl sample for the CE analysis of released N-glycans. Taking the LoD value into consideration for selecting the optimal biological sample source, blood had to be excluded due to its very low PSA concentration. Standard PSA-ELISA tests of our urine samples resulted in an average concentration of 60 ng/ml with a maximum of 120 ng/ml and a minimum of 30 ng/ml, which was slightly lower comparing to literature data (Bolduc et al., 2007). Results varied on a high scale between the samples from different test subjects as well as from the same test subject but different donation dates. The PSA-ELISA method was developed for testing blood PSA level, thus a female urine sample was also processed as negative control, resulting in 0 ng/ml PSA. Female urine was also spiked with standard PSA for positive control, resulting in the expected concentration. Control results suggested that the urine matrix did not affect the accuracy of PSA-ELISA tests. Considering the lowest concentration, a minimum requirement was 150 ml of urine to reliably obtain sufficient quantity of PSA for capture and analysis.

Figure 4:
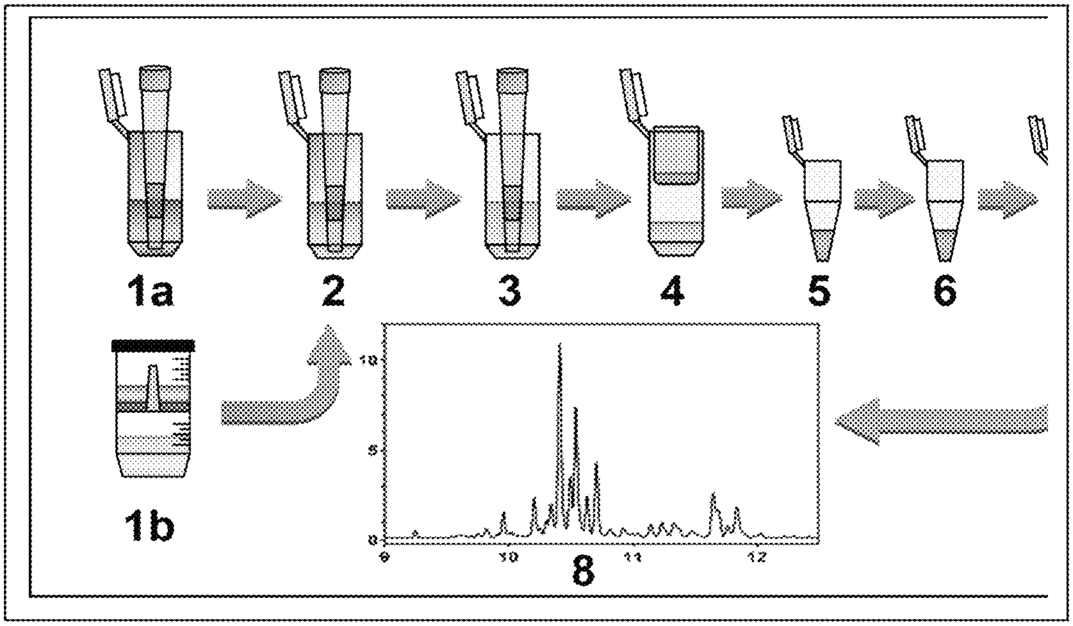
FIG. 4. Urinary PSA analysis workflow. 1a) Immobilization of aPSA sdAbs to Ni-IMAC column; 1b) Concentration of urine via spinfilters; 2) PSA capture from urinary matrix; 3) Elution of antibody-PSA complex; 4) Desalting and concentration; 5) Denaturation of PSA; 6)N-glycan release by PNGase F digestion; 7) Fluorescent glycan labeling; 8) CE-LIF analysis FIG. 5. Capillary electrophoresis separation of the sdAb captured male urinary PSA N-glycome (B) and female urine control (A). Separation conditions: 30 cm total (20 cm effective) length, 50 μm i.d. bare fused silica capillary with HR-NCHO gel buffer. Voltage: 30 kV (0.5 min ramp); Temperature: 25° C.; Injection: 5 psi/5 sec water pre-injection followed by 2 kV/2 sec sample. Structures corresponding to peaks are listed in Table 1.

To immobilize the aPSA sdAbs, Ni-IMAC microcolumns were chosen (FIG. 4/1*a*) as they showed strong affinity for the histidine tags of the nanobodies. In order to effectively introduce all of the biological matrix to the column, the volume of urine had to be reduced to the 1 ml scale (i.e., to fit in a 1000 μL pipette tip based affinity columns). Simple evaporation of the water content of the samples was problematic as the higher temperature could lead to possible loss of sensitive sialic sugar structures and precipitation. Therefore, 10 kDa cut-off value filters were utilized (FIG. 4/1*b*), which could retain PSA effectively, while letting through the solvent and small contaminants (e.g., sugars). Changing the urinary matrix to buffer was beneficial in multiple levels. It contributed to avoid any possible undesirable effect on the sdAb capture due to the variable urinary pH as well as introduced imidazole as an inhibiting agent to prevent non-specific bindings of remaining (>10 kDa) urine components.

As capturing agent, both variants C9 and N7 of aPSA capturing capabilities were tested. Despite the different equilibrium binding constants, they resulted in equally high yields in terms of signal intensity in CE analysis, when their binding capacities were tested in preliminary experiments by standard PSA capture from buffer solution (data not presented). Eventually, our final choice was the C9 variant, as it provided slightly higher yields during both production and capture. Various methods were also tested during the elution step (FIG. 4/3) (denaturation, EDTA, etc.) and 500 mM imidazole proved to be the best for removing the nanobody-antigen complex from the column. Because *E. coli* is unable to glycosylate proteins, thus, sdAbs were not glycosylated, i.e., there was no need for their removal from the sample. However, changing the buffer for water was required after the elution (FIG. 4/4) as the high salt concentration interfered with the removal of excess labeling dye later in the sample preparation workflow.

Figure 5:
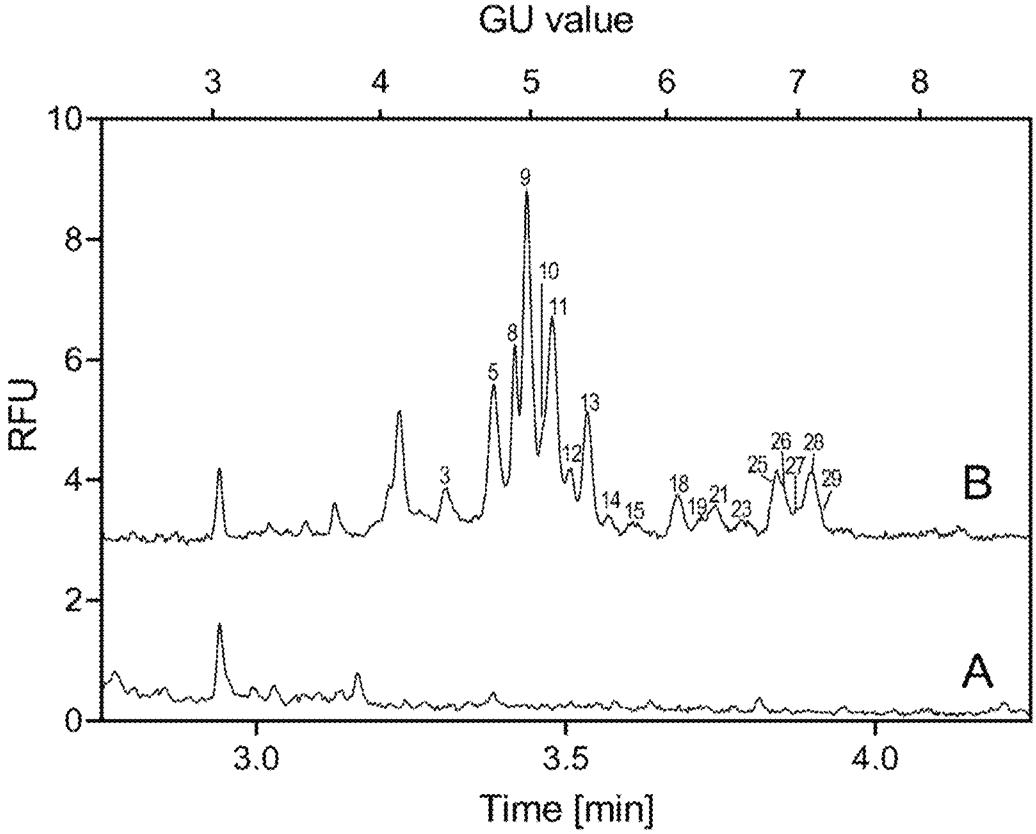

The initial test of the capturing method was facilitated with standard PSA spiked into buffer solution. The glycan profile of captured PSA was corresponding to the standard PSA profile. To evaluate the matrix effect of urine, standard PSA was also spiked into and then captured from female urine, resulting similar yields in analytical signal compared to the spiked buffer, as well as, similar glycan profile as of the standard PSA, suggesting that sdAb were not affected negatively by the matrix. The results of concentrated and captured male urine were also corresponding with both spiked variants. To verify that all the resulted glycans were originated from urinary or spiked PSA, unspiked female urine was used as a control, in which case no glycan related peaks were detected. Each glycan profile is shown in FIG. 5. From concentrated and captured male urine 19 corresponding structure was identified and their peak area distribution was also similar to the standard. Please note that 20 cm effective length capillary was utilized for the separation of the captured urinary PSA glycans as we aimed the development of a fast, high-throughput method, which can be readily adapted into the clinic. No desialylated glycans were found, proving that both the analytical tool and the selective capture procedure provided sufficiently mild conditions to preserve sensitive sugar structures, e.g., sialic acids. As with the standard PSA, the α2,3- and α2,6-sialylated isomers were separated on both mono- and multi-sialylated structures, as well as, the core fucosylated or bisecting structures.

REFERENCES

Adamczyk, B., Tharmalingam, T., & Rudd, P. M. (2012). Glycans as cancer biomarkers. In *Biochimica et Biophysica Acta—General Subjects* (Vol. 1820, Issue 9, pp. 1347-1353). Elsevier. https://doi.org/10.1016/j.bbagen.2011.12.001

Arbabi-Ghahroudi, M. (2017). Camelid single-domain antibodies: Historical perspective and future outlook. *Frontiers in Immunology,* 8(NOV), 1589. https://doi.org/10.3389/fimmu.2017.01589

Armbruster, D. A. (1993). Prostate-specific antigen: Biochemistry, analytical methods, and clinical application. In *Clinical Chemistry*. https://doi.org/10.1093/clinchem/39.2.181

Bessette, P. H., Åslund, F., Beckwith, J., & Georgiou, G. (1999). Efficient folding of proteins with multiple disulfide bonds in the *Escherichia coli* cytoplasm. *Proceedings of the National Academy of Sciences of the United States of America*. https://doi.org/10.1073/pnas.96:24.13703

Bolduc, S., Lacombe, L., Naud, A., Grégoire, M., Fradet, Y., & Tremblay, R. R. (2007). Urinary PSA: A potential useful marker when serum PSA is between 2.5 ng/ml and 10 ng/ml. *Journal of the Canadian Urological Association,* 1(4), 377-381. https://doi.org/10.5489/cuaj.444

Carlsson, S. V., & Vickers, A. J. (2020). Screening for Prostate Cancer. *In Medical Clinics of North America*. https://doi.org/10.1016/j.mcna.2020.08.007 dos Santos Silva, P. M., Albuquerque, P. B. S., de Oliveira, W. F., Coelho, L. C. B. B., & dos Santos Correia, M. T. (2019). Glycosylation products in prostate diseases. In *Clinica Chimica Acta*. https://doi.org/10.1016/j.cca.2019.08.003

Ferens-Sieczkowska, M., Kowalska, B., & Kratz, E. M. (2013). Seminal plasma glycoproteins in male infertility and prostate diseases: Is there a chance for glyco-biomarkers? In *Biomarkers*. https://doi.org/10.3109/1354750X.2012.719035

Filella, X., Fernández-Galan, E., Bonifacio, R. F., & Foj, L. (2018). Emerging biomarkers in the diagnosis of prostate cancer. In *Pharmacogenomics and Personalized Medicine* (Vol. 11, pp. 83-94). Dove Medical Press Ltd. https://doi.org/10.2147/PGPM.S136026

Gasteiger, E., Hoogland, C., Gattiker, A., Duvaud, S., Wilkins, M. R., Appel, R. D., & Bairoch, A. (2005). Protein Identification and Analysis Tools on the ExPASy Server. In *The Proteomics Protocols Handbook*. https://doi.org/10.1385/1-59259-890-0:571

Gebauer, M., & Skerra, A. (2019). Engineering of binding functions into proteins. *Current Opinion in Biotechnology,* 60, 230-241. https://doi.org/10.1016/j.copbio.2019.05.007

Gilgunn, S., Conroy, P. J., Saldova, R., Rudd, P. M., & O'Kennedy, R. J. (2013). Aberrant PSA glycosylation-A sweet predictor of prostate cancer. In *Nature Reviews Urology*. https://doi.org/10.1038/nrurol.2012.258

Gilgunn, S., Murphy, K., Stöckmann, H., Conroy, P. J., Brendan Murphy, T., William Watson, R., O'kennedy, R. J., Rudd, P. M., & Saldova, R. (2020). Glycosylation in indolent, significant and aggressive prostate cancer by automated high-throughput n-glycan profiling. *International Journal of Molecular Sciences*. https://doi.org/10.3390/ijms21239233

Guttman, A., & Ulfelder, K. W. (1997). Exoglycosidase matrix-mediated sequencing of a complex glycan pool by capillary electrophoresis. *Journal of Chromatography A,* 781 (1-2), 547-554. https://doi.org/10.1016/S0021-9673(97) 00724-3

Kammeijer, G. S. M., Jansen, B. C., Kohler, I., Heemskerk, A. A. M., Mayboroda, O. A., Hensbergen, P. J., Schappler, J., & Wuhrer, M. (2017). Sialic acid linkage differentiation of glycopeptides using capillary electrophoresis-Electrospray ionization-Mass spectrometry. *Scientific Reports*. https://doi.org/10.1038/s41598-017-03838-y Kammeijer, G. S. M., Nouta, J., De La Rosette, J. J. M. C. H., De Reijke, T. M., & Wuhrer, M. (2018). An In-Depth Glycosylation Assay for Urinary Prostate-Specific Antigen. *Analytical Chemistry. https://doi.org/*10.1021/acs.analchem.7604281

Kyselova, Z., Mechref, Y., Al Bataineh, M. M., Dobrolecki, L. E., Hickey, R. J., Vinson, J., Sweeney, C. J., & Novotny, M. V. (2007). Alterations in the serum glycome due to metastatic prostate cancer. *Journal of Proteome Research*. https://doi.org/10.1021/pr060664t Levy, R., Weiss, R., Chen, G., Iverson, B. L., & Georgiou, G. (2001). Production of correctly folded fab antibody fragment in the cytoplasm of *Escherichia coli* trxB gor mutants via the coexpression of molecular chaperones. *Protein Expression and Purification*. https://doi.org/10.1006/prep.2001.1520

Lynne, C. M., Aballa, T. C., Wang, T. J., Rittenhouse, H. G., Ferrell, S. M., & Brackett, N. L. (1999). Serum and semen prostate specific antigen concentrations are different in young spinal cord injured men compared to normal controls. *Journal of Urology,* 162(1), 89-91. https://doi.org/10.1097/00005392-199907000-00022

Mészáros, B., Járvás, G., Farkas, A., Szigeti, M., Kovács, Z., Kun, R., Szabó, M., Csánky, E., & Guttman, A. (2020). Comparative analysis of the human serum N-glycome in lung cancer, COPD and their comorbidity using capillary electrophoresis. *Journal of Chromatography B: Analyti-*

*cal Technologies in the Biomedical and Life Sciences*. https://doi.org/10.1016/j.jchromb.2019.121913

Munkley, J., Mills, I. G., & Elliott, D. J. (2016). The role of glycans in the development and progression of prostate cancer. In *Nature Reviews Urology*. https://doi.org/10.1038/nrurol.2016.65

Muyldermans, S. (2021). A guide to: generation and design of nanobodies. *FEBS Journal,* 288(7), 2084-2102. https://doi.org/10.1111/febs.15515

Peracaula Miró, R., Aleixandre Cerarols, R. N., Barrabés Vera, S., Comet Batlle, J., De Llorens Duran, R., Fahey, R., Ferrer Batallé, M. L., Escorihuela, E., Ramírez Malagón, M., & Rudd, P. M. (2017). IN VITRO METHOD FOR DIAGNOSING PROSTATE CANCER (Patent No. WO2017077162A1). https://worldwide.espacenet.com/patent/search/family/058662301/publication/WO2017077162A1?q=pn % 3DWO2017077162A1

Pihíková, D., Kasák, P., & Tkac, J. (2015). Glycoprofiling of cancer biomarkers: Label-free electrochemical lectin-based biosensors. In *Open Chemistry* (Vol. 13, Issue 1, pp. 636-655). De Gruyter Open Ltd. https://doi.org/10.1515/chem-2015-0082

Pinsky, P. F., Kramer, B. S., Crawford, E. D., Grubb, R. L., Urban, D. A., Andriole, G. L., Chia, D., Levin, D. L., & Gohagan, J. K. (2006). Prostate volume and prostate-specific antigen levels in men enrolled in a large screening trial. *Urology*. https://doi.org/10.1016/j.urology.2006.02.026

Reider, B., Jarvas, G., Krenkova, J., & Guttman, A. (2020). Separation based characterization methods for the N-glycosylation analysis of prostate-specific antigen. *Journal of Pharmaceutical and Biomedical Analysis,* 113797. https://doi.org/10.1016/j.jpba.2020.113797

Saerens, D., Kinne, J., Bosmans, E., Wernery, U., Muyldermans, S., & Conrath, K. (2004). Single domain antibodies derived from dromedary lymph node and peripheral blood lymphocytes sensing conformational variants of prostate-specific antigen. *Journal of Biological Chemistry*. https://doi.org/10.1074/jbc.M409292200

Saldova, R., Fan, Y., Fitzpatrick, J. M., Watson, R. W. G., & Rudd, P. M. (2011). Core fucosylation and α2-3 sialylation in serum N-glycome is significantly increased in prostate cancer comparing to benign prostate hyperplasia. Glycobiology. https://doi.org/10.1093/glycob/cwq147

Shriver, Z., Venkataraman, G., Sasisekharan, R., & Sundaram, M. (2004). *GLYCAN MARKERS FOR DIAGNOSING AND MONITORING DISEASE* (Patent No. WO2004066808A2).

Škrlec, K., Štrukelj, B., & Berlec, A. (2015). Non-immunoglobulin scaffolds: A focus on their targets. *Trends in Biotechnology,* 33(7), 408-418. https://doi.org/10.1016/j.tibtech.2015.03.012

Stern, L. A., Case, B. A., & Hackel, B. J. (2013). Alternative non-antibody protein scaffolds for molecular imaging of cancer. *Current Opinion in Chemical Engineering,* 2(4), 425-432. https://doi.org/10.1016/j.coche.2013.08.009

Szigeti, M., & Guttman, A. (2017). Automated N-Glycosylation Sequencing of Biopharmaceuticals by Capillary Electrophoresis. *Scientific Reports,* 7(1). https://doi.org/10.1038/s41598-017-11493-6

Tkac, J., Bertok, T., Hires, M., Jane, E., Lorencova, L., & Kasak, P. (2019). Glycomics of prostate cancer: updates. In *Expert Review of Proteomics*. https://doi.org/10.1080/14789450.2019.1549993

Tkac, J., Gajdosova, V., Hroncekova, S., Bertok, T., Hires, M., Jane, E., Lorencova, L., & Kasak, P. (2019a). Prostate-specific antigen glycoprofiling as diagnostic and prognostic biomarker of prostate cancer. In *Interface Focus*. https://doi.org/10.1098/rsfs.2018.0077

Tkac, J., Gajdosova, V., Hroncekova, S., Bertok, T., Hires, M., Jane, E., Lorencova, L., & Kasak, P. (2019b). Prostate-specific antigen glycoprofiling as diagnostic and prognostic biomarker of prostate cancer. In *Interface Focus* (Vol. 9, Issue 2). Royal Society Publishing. https://doi.org/10.1098/rsfs.2018.0077

Vashist, S. K., & Luong, J. H. T. (2018). Antibody immobilization and surface functionalization chemistries for immunodiagnostics. In *Handbook of Immunoassay Technologies: Approaches, Performances, and Applications* (pp. 19-46). Elsevier. https://doi.org/10.1016/B978-O-12-811762-0.00002-5

Yoneyama, T., Ohyama, C., Tobisawa, Y., Ishikawa, T., Date, M., & Nakamura, K. (2019). *METHOD FOR DETERMINING PROSTATE CARCINOMA* (Patent No. WO2019221279A1).

Yoneyama, T., Tobisawa, Y., Ishikawa, T., Kurosawa, T., & Nakamura, K. (2017). *Prostate carcinoma determination method* (Patent No. WO2017130578A1). https://worldwide.espacenet.com/patent/search/family/059397997/publication/WO2017130578A1?q=pn % 3DWO2017130578A1

Yoon, K. Y., Son, Y. S., Hong, H. S., & Choi, H. (2011). *KIT FOR DIAGNOSING PROSTATE CANCER AND DIAGNOSIS METHOD* (Patent No. WO2011074802A2). https://worldwide.espacenet.com/patent/search/family/044167817/publication/WO2011074802A2?q=pn % 3DWO2011074802A2

Zhang, H., Meany, D. L., Chan, D. W.-Y., Zhang, Z., Li, Y., & Sokoll, L. J. (2010). *DETECTION OF PROSTATE CANCER USING PSA GLYCOSYLATION PATTERNS* (Patent No. WO2010011357A2).

The invention claimed is:

1. A method for PSA-analysis from urine sample of a male mammal, wherein said method comprises the steps of providing urine sample, preparing said urine sample for analysis, separating PSA from said urine sample by affinity separation using PSA-binding molecules to obtain enriched PSA, releasing glycans from the enriched PSA to obtain released PSA-glycans, labeling the released PSA glycans by a fluorescent dye, to obtain fluorophore labeled released PSA glycans, analyzing the released labeled glycans by separation with capillary electrophoresis (CE) wherein detection of the separated, fluorophore labeled, released PSA glycans is carried out by fluorescent detection.

2. The method according to claim 1, wherein detection of the separated released glycans is carried out by laser induced fluorescence detection.

3. The method according to claim 1, wherein affinity separation is affinity partitioning.

4. The method according to claim 1, wherein preparing said urine sample comprises pre-concentration of the sample.

5. The method according to claim 1, wherein in the affinity-separation step the PSA-binding molecules are nanobodies.

6. The method according to claim 5, wherein the affinity partitioning column is a chromatography microcolumn, wherein the nanobodies have a tag and the chromatography column has a matrix binding said tags.

7. The method according to claim 1, wherein releasing glycans from the PSA to obtain released PSA-glycans is carried out enzymatically.

8. The method according to claim 1, wherein the method comprises analyzing the fluorophore labeled released PSA glycans by separating at least the fucosylated and non-fucosylated glycan structures of the fluorophore labeled released PSA glycans.

9. The method according to claim 1, wherein the method comprises analyzing the fluorophore labeled released PSA glycans by separating at least the α2,3- and α2,6-sialylated isomers of the fluorophore labeled released PSA glycans.

10. A diagnostic method for diagnosing PSA-related condition from urine sample of a male subject, said method comprising the steps of carrying out the method according to claim 1 for PSA-analysis, determining a glycosylation pattern in said urine sample of a patient, i.e. a patient glycosylation pattern, comparing the patient glycosylation pattern with a normal glycosylation pattern, and if there is a difference between the patient glycosylation pattern and the normal glycosylation pattern the patient is considered as having a PSA-related condition.

11. The method according to claim 1, wherein releasing glycans from the PSA to obtain released PSA-glycans is carried out enzymatically with endoglycosidases.

12. The method according to claim 5, wherein in the affinity-separation step the PSA-binding molecules are single-domain antibodies.

* * * * *